(12) United States Patent
Matthiesen et al.

(10) Patent No.: US 10,295,442 B2
(45) Date of Patent: May 21, 2019

(54) TWO PHASE IMMISCIBLE SYSTEM FOR THE PRETREATMENT OF EMBEDDED BIOLOGICAL SAMPLES

(75) Inventors: Steen Hauge Matthiesen, Hilleroed (DK); Søren Nielsen, Aalborg (DK)

(73) Assignee: DAKO DENMARK A/S, Glostrup (DK)

( * ) Notice: Subject to any disclaimer, the term of this patent is extended or adjusted under 35 U.S.C. 154(b) by 1000 days.

(21) Appl. No.: 14/001,714

(22) PCT Filed: Feb. 28, 2012

(86) PCT No.: PCT/IB2012/000405
§ 371 (c)(1),
(2), (4) Date: Nov. 6, 2013

(87) PCT Pub. No.: WO2012/117294
PCT Pub. Date: Sep. 7, 2012

(65) Prior Publication Data
US 2014/0051118 A1    Feb. 20, 2014

Related U.S. Application Data

(60) Provisional application No. 61/447,364, filed on Feb. 28, 2011.

(51) Int. Cl.
G01N 1/30    (2006.01)
G01N 1/31    (2006.01)
G01N 1/36    (2006.01)

(52) U.S. Cl.
CPC .............. *G01N 1/30* (2013.01); *G01N 1/312* (2013.01); *G01N 2001/366* (2013.01)

(58) Field of Classification Search
CPC ....... G01N 1/30; G01N 1/36; G01N 2001/366
See application file for complete search history.

(56) References Cited

U.S. PATENT DOCUMENTS 2,137,549 A    11/1938   Subkow
3,769,934 A    11/1973   Dunn
(Continued)

FOREIGN PATENT DOCUMENTS

CN    201607343 U    10/2010
EP      1793218 A1    6/2007
(Continued)

OTHER PUBLICATIONS

Holloway (1969). The Composition of Beeswax Alkyl Esters. Journal of the American Oil Chemist' Society, v46(4), p. 189-190.*
(Continued)

*Primary Examiner* — Sean C. Barron

(57) ABSTRACT

The present application provides a two phase immiscible system for the pretreatment of embedded biological samples comprising placing at least one support having an embedded biological sample on its surface into a pretreatment container, adding to the pretreatment container at least one reagent forming a layer, adding a carrier composition to the pretreatment container, such that reagent forming layer is formed on the top of the carrier composition, and in an amount such that the at least one reagent forming layer contacts at least a portion of the embedded biological sample. Pretreatment of the embedded biological samples can include removal of embedding medium from embedded biological, target retrieval and enzyme blocking samples before staining histochemical analysis or other processes. The system also includes an apparatus and processes of automation of the pretreatment methods.

22 Claims, 14 Drawing Sheets

(56) References Cited

U.S. PATENT DOCUMENTS

| | | | |
|---|---|---|---|
| 4,379,525 A | 4/1983 | Nowicki et al. | |
| 4,543,236 A | 9/1985 | Von | |
| 5,344,637 A | 9/1994 | Camiener | |
| 5,695,942 A * | 12/1997 | Farmilo | G01N 1/312 422/106 |
| 5,830,413 A | 11/1998 | Lang et al. | |
| 5,948,359 A | 9/1999 | Chang et al. | |
| 6,451,551 B1 * | 9/2002 | Zhan | G01N 1/30 435/40.5 |
| 6,544,498 B1 * | 4/2003 | Takada | A23G 4/126 424/49 |
| 6,544,798 B1 | 4/2003 | Christensen et al. | |
| 6,632,598 B1 | 10/2003 | Zhang et al. | |
| 6,855,559 B1 | 2/2005 | Christensen et al. | |
| 7,468,161 B2 * | 12/2008 | Reinhardt | B01L 9/52 422/536 |
| 2003/0175852 A1 | 9/2003 | Kalra et al. | |
| 2004/0002163 A1 | 1/2004 | Reinhardt et al. | |
| 2005/0064535 A1 * | 3/2005 | Favuzzi | G01N 1/30 435/40.5 |
| 2006/0171857 A1 * | 8/2006 | Stead | B01L 3/502715 422/400 |
| 2006/0190185 A1 | 8/2006 | Ford et al. | |
| 2009/0155907 A1 * | 6/2009 | Winther | G01N 1/30 435/378 |
| 2010/0144018 A1 | 6/2010 | Shah et al. | |
| 2011/0003369 A1 | 1/2011 | Kirsch | |

FOREIGN PATENT DOCUMENTS

| | | |
|---|---|---|
| JP | 60-131442 | 7/1985 |
| JP | 64-73516 | 3/1989 |
| JP | 05-087817 | 4/1993 |
| JP | 08-261896 | 10/1996 |
| JP | 09-043119 | 2/1997 |
| JP | 10-019749 | 1/1998 |
| JP | 2001-290084 | 10/2001 |
| JP | 2002-505420 | 2/2002 |
| JP | 2006-308575 | 11/2006 |
| JP | 2008-507701 | 3/2008 |
| JP | 2008-522192 | 6/2008 |
| JP | 2008-203276 | 9/2008 |
| WO | 99/44030 | 9/1999 |
| WO | 00/14507 | 3/2000 |
| WO | 01/73399 | 10/2001 |
| WO | 02/23156 | 3/2002 |
| WO | 03/089240 | 10/2003 |
| WO | 2005/057180 | 6/2005 |
| WO | 2007/062649 | 6/2007 |

OTHER PUBLICATIONS

Japanese Office Action for Japanese Application No. 2013-555948, dated Dec. 18, 2015 (10 pages).

Office Action issued in Chinese Patent Application No. 201280010677.2, dated Jul. 16, 2015.

English translation of Office Action issued in Chinese Patent Application No. 201280010677.2, dated Jul. 16, 2015.

Chinese Office Action for Chinese Application No. 201280010677.2, dated Mar. 15, 2016 (16 pages).

Rui, Wang, et al., "Influence of Amylases on Retrogradation of Instant Rice," Journal of the Chinese Cereals and Oils Association, vol. 22, No. 4, Jul. 2007 (3 pages).

Palmer-Toy, et al., "Efficient Method for the Proteomic Analysis of Fixed and Embedded Tissues," Journal of Proteome Research, 2015, vol. 4, pp. 2404-2411.

* cited by examiner

TWO PHASE IMMISCIBLE SYSTEM FOR THE PRETREATMENT OF EMBEDDED BIOLOGICAL SAMPLES

This application is a national stage entry under 35 U.S.C. § 371 of International Application No. PCT/IB2012/000405, filed Feb. 28, 2012 which claims priority to U.S. Provisional Application No. 61/447,364, filed Feb. 28, 2011, all of which are incorporated herein by reference in their entirety.

FIELD OF THE APPLICATION

The present disclosure relates to the field of processing of biological samples, and specifically to pretreatment of embedded biological samples, e.g. removal of embedding medium from embedded biological samples before staining, histochemical analysis or other processes. More specifically the disclosure relates to removal of embedding medium from embedded biological samples using a two phase system with a dip tank and skim over process. The present disclosure relates to an efficient and cost effective method and composition for removing an embedding medium in an embedded biological sample.

Sample processing in immunohistochemistry ("IHC") applications, for example, and in other chemical and biological analyses may involve at least one processing sequence or treatment protocol as part of an analysis of at least one sample. Typically, such treatment protocols are defined by organizations or individuals requesting analysis, such as pathologists or histologists attached to a hospital, and may be further defined by the dictates of a particular analysis to be performed.

In preparation for sample analysis, a biological sample may be acquired and mounted on a slide or other carrier usually in some form of preservation. As one example, a sample such as a layer or slice of tissue may be preserved in formaldehyde and embedded in paraffin or other embedding media, and sectioned using a microtome. Tissue sections may then be mounted on a slide. Samples preserved with paraffin may undergo deparaffinization, a process by which paraffin embedding the sample is removed. In addition, the target or sample may undergo target retrieval, a process wherein the target or sample is restored to a condition where it is suitable for staining operations.

The term "staining" refers to a process by which certain parts of a sample are treated in order to reveal or highlight characteristics of the sample. As a result of staining, characteristics sought to be revealed may acquire a different color, either in the optic range or in another electromagnetic range, such as the ultra-violet range. In some instances, staining may lead to a detectable change in properties, such as a change in the fluorescent, magnetic, electrical, or radioactive properties of the sample. Staining of a sample includes a series of treatment steps referred to as a treatment protocol. A typical treatment protocol may include washing, binding of reagents to the specific parts of the sample, any activation of the reagents, and each treatment step may include a plurality of individual treatments.

Diagnostic applications, for example immunohistochemistry (IHC), in situ hybridization (ISH) and special stains, may involve processing sequences or treatment protocols that comprise steps such as deparaffinization, target retrieval, and staining. In some applications, these steps may have been performed manually, potentially creating a time-intensive protocol and necessitating personnel to be actively involved in the sample processing. Even when performed automatically, there have been insufficiencies in such applications. Attempts have been made to automate sample processing to address the need for expedient sample processing and a less manually burdensome operation.

In order to preserve biological samples for future analysis, different kinds of embedding media have been used. An "embedding medium" may be any composition that is solid at room temperature and is used in histology for embedding or otherwise supporting biological samples for histological or other analyses, such as immunohistochemistry, in situ hybridization, special stains, and classical dye stains. Examples of embedding media include, but are not limited to, wax, paraffin, paramat, paraplats, peel away paraffin, tissue freezing medium, cryonic gel, OCT™ ("Optimum Cutting Temperature") embedding compound, Polyfin™, polyester wax.

A "wax" may be a composition for embedding biological samples for histochemical or other chemical and biological analyses. Wax is solid at room temperature; usually consists of a complex mixture of higher hydrocarbons often including esters of higher fatty acids and higher glycols; may be mineral, natural or synthetic in origin; is harder and more brittle than fats; is soluble in oils and fats, and can optionally contain additives that enhance its sample-embedding properties. Paraffin is an example of a mineral wax most commonly used in the histochemical field. Paraffin is a hydrophopic substance typically prepared by distillation of petroleum, and is a mixture of primarily solid saturated hydrocarbons. The paraffin (wax) generally consists of higher polyolefins and often comprises polymers or dimethyl sulfoxide ("DMSO") is added.

Paraffin has been used for many years as an embedding medium in the preparation of biological samples for sectioning in a microtome to produce sample sections for histological examination.

As used in this disclosure "histochemical" generally refers to the techniques and methods known as immunohistochemistry, cytochemistry, histopathology, special stains, microtechniques, and the use of molecular probes such as in situ hybridization.

As used in this disclosure, the term "deparaffinization" encompasses the removal of paraffin or other embedding media described in the present application. Deparaffinization, prior to staining, is usually required to allow access to targets for antibodies or probes in a subsequent staining process. Solvents used for deparaffinization are, for example, xylene, xylene substitutes and toluene. The solvents generally used in deparaffinization may be toxic, flammable and pose environmental hazards.

Traditional manual deparaffinization procedures include, for example, the steps of immersing the embedded sample in a xylene (Fisher Scientific, Cat. #X5-4) bath, toluene bath or a Histo-Clear® (National Diagnostics Inc., Cat. # HS-200) bath until the embedding medium is solubilized. The deparaffinized sample is subsequently washed and rehydrated in order to remove solvent and rehydrate the sample with a series of alcohol solutions of decreasing alcohol concentration, typically as baths in which the sample is immersed. The sample may, for example, be rehydrated by immersing it twice in a first bath of 95% ethanol, twice in a second bath of 70% ethanol, and a third bath of an aqueous buffer.

The flash point of a fuel is the lowest temperature at which it can form an ignitable mix with air. At this temperature the vapor may cease to burn when the source of ignition is removed. A slightly higher temperature, the fire point, is defined as the temperature when vapor continues to burn after being ignited. As mentioned above, xylene is a flammable, volatile and toxic organic solvent; xylene has a low boiling point of about 137 degrees C., a low flash point of about 29 degrees C., and a low explosive limit ranging from 1 to 6%. Similarly, alcohol, and especially ethanol is flammable and has a low boiling point of about 78 degrees C., a low flash point of about 17 degrees C., low explosive limits ranging from 3.5 to 15% and can therefore easily form part in an explosive air mixture. However, diluted alcohol solutions, such as 10% or 20% ethanol in water, can have significantly higher flash point and boiling point than the ethanol solutions traditionally used (70-95% ethanol in water).

Due to the hazardous properties of xylene and alcohol, it would be advantageous to develop safer deparaffinization methods. Efforts have been made to replace xylene in the deparaffinization process with less toxic and less volatile solvents. Terpene oil and isoparaffinic hydrocarbons, for example, have been shown to produce deparaffinization equal to xylene. Nevertheless, even when using these alternative solvents, a series of alcohol washes, also known as a rehydrating process, is still required to remove the solvent prior to the water wash to achieve compatibility with most types of staining, for example immunohistochemical staining.

U.S. Pat. No. 6,632,598, U.S. patent application publication 2003/0175852 A1, and international patent application WO 02/23156 A1 to BioGenex Laboratories describe compositions and methods for removal of wax from wax-embedded biological samples wherein the use of xylene may be eliminated and the use of alcohol in the subsequent washing steps is reduced or eliminated. The compositions described therein comprise a paraffin-solubilizing organic solvent, a polar organic solvent, and a surfactant. Examples of paraffin-solubilizing organic solvents include aromatic hydrocarbons, aliphatic hydrocarbons, terpenes, other oils, and petroleum distillates. The polar organic solvent includes, for example, ketones and lower alcohols. Alcohols may be, for example, ethanol, ethylene glycol, isopropanol, propylene glycol and mixtures thereof.

A drawback of the compositions and methods disclosed by BioGenex Laboratories, is that even if the use of post-deparaffinization alcohol baths may be reduced or eliminated, the polar organic solvent of the deparaffinization compositions disclosed includes alcohol. Therefore, the disclosed deparaffinization compositions have the same drawbacks as the deparaffinization methods using alcohol baths or washes.

U.S. Pat. No. 5,344,637 to Camiener describes a method of using organic ring-containing compounds as solvents instead of Histo-Clear® and Xylene. The solvents are used to replace the alcohol and/or other dehydrants in fixed biological materials and to remove wax from wax-embedded biological materials. The solvent comprises from 5% to 100%, by weight, of a compound selected from the group consisting of unsubstituted and substituted derivatives of saturated, organic ring-containing compounds, either alone, or present in hydrogenated aromatic petroleum distillates, and in combination thereof. The solvent is sold by CBG Biotech under the trade mark Formula 83™. A drawback with Formula 83™ is its fairly low boiling point at 119 to 145 degrees Celsius and general flammability. With a low flash point of only 7 degrees C., and a lower explosive limit (LEL) at only 1.3 vol %, i.e. at a temperature above 7 degrees C., Formula 83™ may form an ignitable mix with air, thus creating a hazardous condition. Further, Formula 83™ is a blend of organic solvents and personal safety precautions should be taken, e.g. gloves and safety goggles should be used.

U.S. patent application publication 2004/0002163 and international patent application publication WO 03/089240 A1 to Ventana Medical Systems, Inc. describe an automated slide staining system for application of stains to biological tissue sections mounted on microscopic slides. The tissue samples are deparaffinized by contacting the sample with a deparaffinizing fluid at a temperature above the melting point of the paraffin embedding the tissue sample. The liquefied paraffin is then rinsed away. The deparaffinizing fluid is an aqueous-based fluid and typically heated to a temperature between 60-70 degrees C., when the embedding medium is paraffin having a melting point between 50-57 degrees C.

U.S. Pat. No. 6,855,559 and U.S. Pat. No. 6,544,798, and international patent application publications WO 99/44030 and WO 00/14507 to Ventana Medical Systems, Inc. disclose removal of embedding medium, without the use of organic solvents, by heating one side of the sample such that the sample slide is dried and the embedding medium is solubilized. The solubilized embedding medium is thereafter washed off. The embedding medium is removed from biological samples on automated instruments prior to immunohistochemical ("IHC"), in situ hybridization ("ISH") or other histochemical or cytochemical manipulations.

According to the disclosure of WO 99/44030, the deparaffinization of the embedded tissue is achieved by precisely controlled heating of individual slides allowing the paraffin embedded in the tissue to melt out and float in aqueous solution where it can be rinsed away. The heating is accomplished by means of thermal platforms arranged radially about the perimeter of a slide carousel upon which the slides with tissue samples may be placed.

Removal of the embedding medium using heat is also disclosed in the international application WO 2005/057180 to Torstein Ljungmann et al.

A drawback with methods and systems using heating for removing embedding medium is that it may be a slow process, since a paraffin embedded biological sample has to be subjected to elevated temperatures during a time period ranging from 5 minutes to 60 minutes. Another drawback is the presumed low efficiency in removing the last paraffin residues in the tissue sections. Yet another drawback is that the heating element used requires that sufficient contact is maintained between the surface on which the biological sample is placed and the heating element.

One aspect of the present application is to provide an improved method of deparaffinization compared to known methods.

According, one objective of the present application is to reduce the risks of fire and explosion during, for example, processing of biological samples in the laboratory. Fire, waste, workers' safety, etc., may be relevant factors in complex automated instruments with various moving robots and electrical circuits, as well as in labs with undertrained personnel. This disclosure also aims to reduce the need for ventilation and airflow in the laboratory Further, one embodiment of the present disclosure aim to provide a simplified method for a vertical mode of operation using a two immiscible phase system where the slides are treated vertically with a minimum volume of an upper layer, and a lower or carrier layer. Accordingly, it is yet another objective of the present disclosure to provide simpler automation of the method for pretreatment of embedded samples for histochemical analysis, that results in cost reduction and improved environmental conditions because of among other things, the use of reduced amount of solvent.

In one embodiment of the present application, there is disclosed a removal method which leaves little or no residues of embedding medium on the slide, and that removes different kinds of embedding medium. For example, in the case of paraffin, the various paraffin sections can originate from various paraffin types and mixtures. Since these residues of embedding medium may hamper the staining and the morphological pattern and information it is advantageous to have one method that removes the different residues. This is desirable as paraffin residues left in a sample can cause problems for ISH methods, and as IHC is becoming more quantitative and standardized, any embedding medium residues may lower or alter the staining intensity, resulting in wrong interpretations.

Embodiments of this disclosure also aim to provide a simplified method for removal of embedding medium from embedded biological samples as compared to existing procedures. Furthermore, embodiments aim to automate the processing and minimize manual handling.

In another embodiment of the present application, there is disclosed a method for deparaffinization using a solvent, which does not require a subsequent step of rehydration before target retrieval. In another embodiment of the present application, there is disclosed a method and apparatus for performing deparaffinization, rehydration and target retrieval in one chamber.

Further, embodiments of the present disclosure aim to provide a simplified method for a vertical mode of operation using a two immiscible phase system where the slides are treated vertically with a minimum volume of an upper layer, and a lower or carrier layer. Accordingly, it is yet another objective of the present disclosure to provide simpler automation of the method for pretreatment of embedded samples for histochemical analysis, that results in cost reduction and improved environmental conditions because of, among other things, the use of a reduced amount of solvent.

SUMMARY

Embodiments of the present application fulfill the aforementioned objectives by, for example, removing the embedding medium using an efficient, non-toxic organic solvent, as well as allowing the user to go directly to aqueous buffers without having to further treat the biological sample with multiple washes with a polar organic solution, such as alcohol (i.e. rehydration).

Another embodiment of the present application provides a method of removing embedding medium from an embedded biological sample using a much smaller amount of organic solvent compared to existing procedures. Hence, for economical reasons it is not necessary to consider reusing the solvent.

The present inventors have realized it is possible to go directly to aqueous buffers from deparaffinization without the use of a polar organic solution such as alcohol. Known methods using organic solvents attempt to gradually change from a pure organic phase to an aqueous phase after deparaffinization by using solvents (e.g. alcohol) that are compatible with both phases. In contrast, the present application uses a two phase system and does not use an alcohol that is miscible with both phases.

The inventors have further realized that it is possible to use a simplified, fast and automated two phase system of a solvent for removal of the embedding media and aqueous washing solution to obtain, for example, dewaxing results equal to or better than traditional methods using solvents.

Moreover, the inventors have further realized that solid embedding media, like paraffin, can be quickly dissolved by lowering their melting point by diffusing a solvent into the solid surfaces. The process can be done at temperatures different or even far from the original melting point of the embedding medium, such as room temperature.

The present application is directed to a method, an apparatus, and use of a two phase system with a solvent for removal of an embedding medium from an embedded biological sample in accordance with the independent claims. Further embodiments are defined in the dependent claims.

In another embodiment of the present application the removal of the embedding media, rehydration, and target retrieval of the biological samples, is followed by application of a reagent to block endogenous peroxidase activity. In another embodiment of the present application the removal of the embedding media, rehydration, and target retrieval of the biological samples, along with the application of a reagent to block endogenous peroxidase activity are combined into a single operation. Such embodiment may be referred to as a 4-in-1 method.

BRIEF DESCRIPTION OF THE DRAWINGS

The accompanying drawings, which are incorporated in and constitute a part of this specification, illustrate a number of non-limiting embodiments of the application, and together with the description, serve to explain the principles the application.

DETAILED DESCRIPTION

Figure 1:
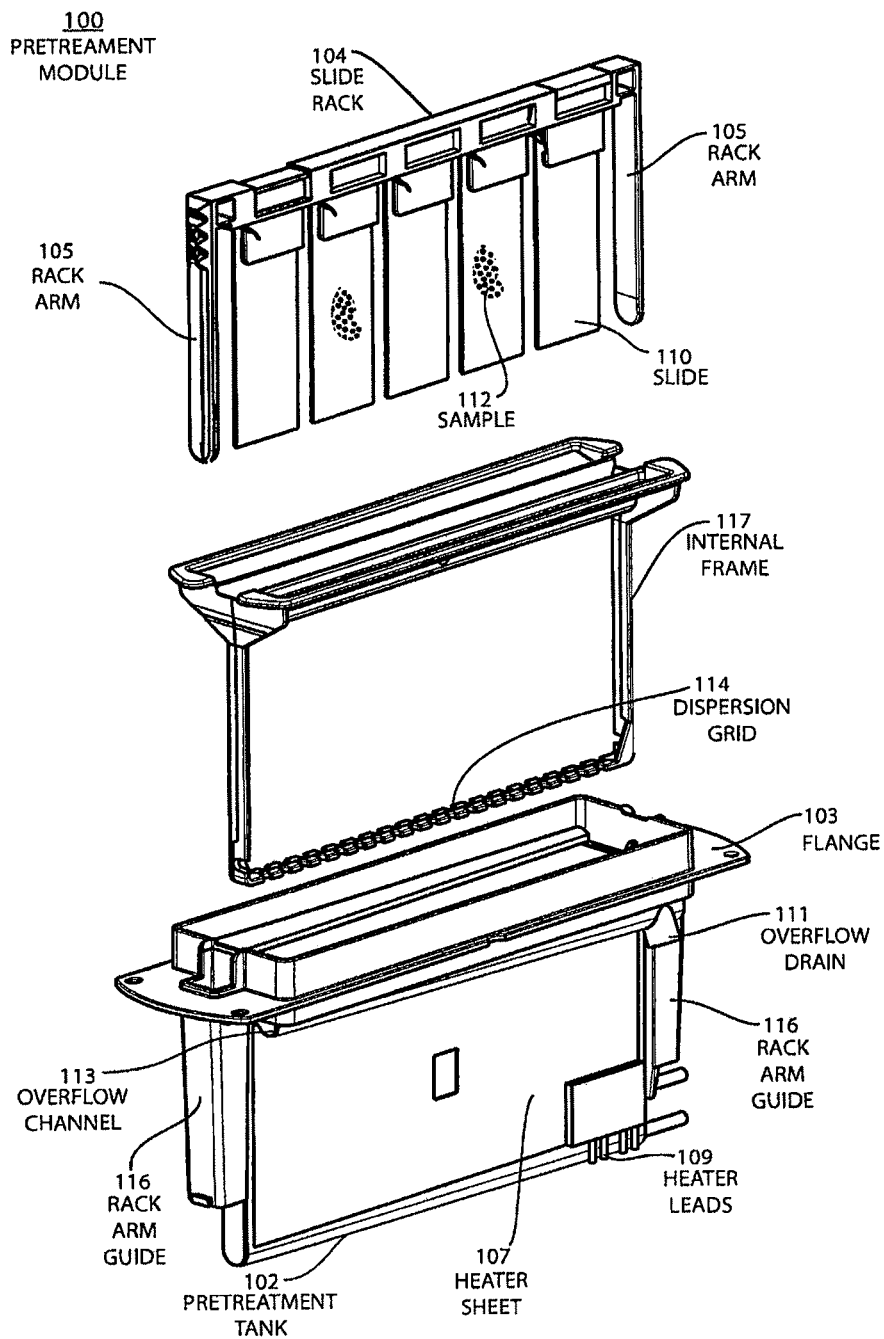
FIG. 1 shows an exploded view of a pretreatment module for the automatic pretreatment and processing of biological samples.

The simple yet effective method disclosed herein is based on the transport of a reagent forming layer over the surface of an embedded biological sample, thereby removing the embedding medium. The reagent forming layer lies on top of a carrier composition, where the carrier composition does not take part in dissolving the paraffin. This two phase system is formed as the two solutions are immiscible. In the content of the present application the term "immiscible" is to be understood as incapable of mixing or attaining homogeneity, i.e. the two solutions when brought together are essentially incapable of homogenous mixing.

The reagent forming layer has a lower density than the carrier composition and, hence, forms the upper phase of the two phase system. This layer may also be referred to as "upper layer" or "second phase layer" in the present disclosure. In embodiments where the reagent forming layer is a solvent, it may also be referred to as the "solvent layer." The carrier composition serves as the first phase of the two phase system and may be referred to as "lower layer", "first phase layer", or "solvent carrier layer."

As used in this application, "biological sample" generally refers to any collection of cells, either loose or in a tissue, which can be mounted on a support. Non exhaustive examples include section of organs, tumor sections, bodily fluids, smears, frozen sections, blood, cytology preps, microorganisms and cell lines.

A "support" generally refers to any medium where at least one biological sample may be placed for further analysis. This includes any support, such as a test tube, chip, array, disk, or slide, e.g. a microscope slide. As used herein a "sample holder" includes any support, such as a carrier, test tube, chip, array, disk, or slide, e.g. a microscope slide, which can support at least one biological sample.

A "sample holder" or "support holder" may also include a device capable of supporting a group of supports, such as a rack that may hold a group of slides.

"Sample holder" may also refer to a larger scale support, such as a slide rack holder that holds at least one smaller support, such as a plurality of slide racks, each rack containing a plurality of slides. A holder may releasable, fixed, and/or held in such a way that permits movement, such as vertical, horizontal or pivoting about one or more axis. In one embodiment, the sample holder may function as a sample holding means. Alternative examples of a sample holder include carousels, trays, racks, carriers, holders, compartments, or other conveyance arrangements used for the handling and processing of samples and sample carriers any of which may be at least partially removable.

As used herein "removing the embedding medium" or "removal of embedding medium" refers to the removal of a sufficient amount of the embedding medium from the embedded biological sample so as to permit the sample to be subjected to further processing and/or analysis. Typically such analysis is histological, e.g. immunohistochemical or in situ hybridization, and the amount of embedding medium that should be removed will be the amount sufficient to permit the analysis technique of choice to gain access to at least one of the reactive sites in the sample. When the embedding media is wax or paraffin, this process may be also referred to as "dewaxing" or "deparaffinization."

The two phase system is a pretreatment system where relatively small volumes of solvent can be used for the removal of embedding medium, such as paraffin, from embedded biological samples. For example a reagent that removes an embedding medium, e.g. Histoclear II®, may be added on top of a carrier composition. The carrier composition can be deoinized water ("DI-water") or target retrieval buffer, for example. The solvent (e.g. Histoclear II® or Clearify™) has a lower density than water and will therefore float on top of the water, thereby creating a liquid two phase system.

The method may be carried out by placing a support or sample holder having an embedded biological sample on its surface into a container, and introducing into the pretreatment tank or container the reagents of the two phase system. During deparaffinization the volume of the carrier composition is changed. For example the volume of the carrier composition may be increased, causing the upper layer of solvent to be transported towards the top or upper end of the container or pretreatment tank and, hence, steadily swept over the embedded biological sample. In one embodiment the layer of solvent partially covers the embedded biological sample at once. In a further embodiment the layer of solvent fully covers the embedded biological sample at once.

In one embodiment of the present application the two phase system provides an improved method and apparatus for deparaffinization of embedded samples. It is beneficial that the two phases are in moving contact with the sample. When the solvent first comes in contact with the paraffin it starts to dissolve it. The movement of the solvent can help pull some of the paraffin off the sample. Thereafter the carrier composition comes into contact with the sample and remains of solvent and/or paraffin, and washes the solvent and/or paraffin off. Any washed solvent and/or paraffin will float and mix with the upper phase. This process may be repeated a number of times, if necessary, until optimum deparaffinization and washing of the sample is achieved.

According to one embodiment of the present application the process can be repeated three times, i.e. once up the slide, then down the slide, then up the slide and into the overflow. It is also possible to repeat the process additional times if necessary, depending on the type of sample and embedding medium. It is also possible to the process fewer times, for example only once, i.e. moving the solvent layer up the slide and into the overflow.

In one embodiment of the present application the removal of the embedding media, rehydration, and target retrieval of the biological samples, is accomplished by three independent processes, possibly followed by application of a reagent to block endogenous peroxidase activity. This can be done using the two phase deparaffinization system of the present application. The reagent to block endogenous peroxidase activity can be added to the carrier composition. Hence, when the solvent for dissolving the embedding medium has swept over the sample for the last time, the carrier composition including the blocking agent comes in contact with the sample and the activity of the endogenous peroxidase is essentially blocked. As previously mentioned the step of rehydration is not necessary when using the two phase system, so the sample can proceed directly to target retrieval.

In another embodiment of the present application the removal of the embedding media, rehydration, and target retrieval of the biological samples, along with the application of a reagent to block endogenous peroxidase activity are combined into a single step. Such embodiment may be referred to as a 4-in-1 method.

A non-solvent based procedure, often called 3-in-1, is commonly used in immunohistochemistry in relation to target retrieval of epitopes in formalin fixed, paraffin embedded tissue samples. The 3-in-1 procedure includes the use of a single reagent (e.g. DAKO; S2375) for the steps of deparaffinization, rehydration, and heat-induced epitope-retrieval (HIER) of the formalin-fixed, paraffin-embedded tissue sections prior to staining. The 3-in-1 reagent is brought into contact with the embedded sample, and the reagent and/or sample is heated to above the melting point of the embedding medium. The embedding medium melts and can be removed from the sample.

When performing the 3-in-1 process in a container or pretreatment tank, the apparatus and method of the present application can be used to remove the melted embedding medium from the container or pretreatment tank, without the embedding medium coming into contact with the sample again. This is advantageous because if the removed embedding medium came into contact with the sample again it would possibly leave residues of embedding medium on the sample. The melted embedding medium has a density lower than the density of the 3-in-1 reagent, therefore it floats on top of the 3-in-1 reagent forming a two phase system. The top layer (i.e. the embedding medium) is then removed from the container or pretreatment tank by overflow as described herein, and according to the methods and apparatus of the present application.

In another embodiment of the application, deparaffinization, rehydration, target retrieval and the application of a reagent to block endogenous peroxidase activity may be combined into a single process in a single reagent, also called 4-in-1. The 4-in-1 reagent is similar to the 3-in-1, i.e. it can perform the steps of deparaffinization, rehydration and target retrieval, but additionally it includes the step of endogenous peroxidase blocking. Peroxidase can influence staining where another peroxidase, such as horseradish peroxidase (HRP) is used in the staining, as they catalyze the same substrate. A traditional 3-in-1 process and reagent would not involve the enzyme blocking step, which prolongs the assay time and thus increases the assay cost, both for automation and manual performance. The traditional 3-in-1 for manual performance would also involve increased hands-on time needed for the enzyme blocking step. Application of the 4-in-1 means that the heating step previously only used to retrieve immunological targets, now includes deparaffinization, rehydration, target retrieval and peroxidase block.

The 4-in-1 reagent for immunohistochemistry reduces the number of steps involved, when compared to the traditional independent unit operations. Also, the 4-in-1 buffer allows the four steps to be performed simultaneously which reduces the assay time. The assay time may be reduced for fully automated, semi-automated, and for manual performed assays. In manual performed assays, there is also a reduction in the hands-on time needed. The 4-in-1 method may be used with any heating device used for heat induced epitope recovery. Typically performing these steps in a traditional sequence will take between 40 to 60 minutes. Using the 4-in-1, the total assay time may be reduced to, for example, 20 to 40 minutes. This time could be used to either heat the slides in the 4-in-1 buffer. The reduction in process time would enable laboratories to perform two or more runs of immunohistochemical assays within one working day. The reduction in process time would also improve the work flow of the assays. The 4-in-1 process may be used, for example, with target retrieval buffers S2367 and S1699 from DAKO.

In at least one embodiment, the 4-in-1 process may involve first the baking of the slides, then heating the slides in the 4-in-1 buffer, for example, for about 20 to 40 minutes, and then performing the immunohistochemical assay. For example, in a standard immunohistochemical process, the deparaffination in xylene may be done twice and take about 5 minutes each time, then rehydration in alcohols may be done four times, and take about 5 minutes each time, then the heat induced epitope retrieval, for example for about 20 to 40 minutes, then the enzyme blocking may take about 10 minutes, then the immunohistochemical assay is performed.

In at least one embodiment of the present application, sections of paraffin embedded tissue are placed directly in a container containing the 4-in-1 buffer and heated. Heat may be supplied to the process by devices and methods generally known in the art, for example, a water bath. After heating, the slides are washed in a wash buffer and can be subsequently processed accordingly to the immunohistochemical procedure used by the laboratory. By using the 4-in-1 reagent, the endogenous peroxidase will be efficiently blocked and simultaneously the paraffin on the sections will be melted and washed away during the post-heating wash step. In at least one embodiment, hydrogen peroxide in concentrations of from 0.075%-0.00005%, for example in the range of 0.075%-0.0000025%, was successfully used. Although use of hydrogen peroxide as an inhibitor has been previously attempted, the results were unsatisfactory until the concept of adding very low concentrations was invented, as disclosed herein.

In another embodiment of the present application, a post staining clearing process is implemented to further reduce the likelihood of paraffin or solvent residue in the sample. According to such embodiment the stained specimen or biological sample is further exposed to a composition capable of dissolving any residues. For example, the stained biological sample maybe exposed to a solvent capable of dissolving any paraffin medium prior to cover slipping.

Embodiments of the present application also relate to a system, apparatus, composition and method for processing of biological samples, and especially to the pretreatment of embedded biological samples by, for example to the removal of embedding medium from embedded biological samples by means of a solvent.

The present application is further directed to software and hardware for the control, management, tracking, monitoring, scheduling, and diagnosing of automatic biological sample processing apparatuses. Systems, methods, and apparatuses according to the present application allow for the automatic pretreatment of the biological samples on slides or other carriers or substrates (slides) in an automatic processing apparatus, such as an automatic staining apparatus (stainer) so that the entire processing of the biological samples may be performed automatically in a single instrument.

The solvent, generally has properties, that allow for fast softening, liquefying or dissolving of the embedding medium. The solvent may dissolve, for example, paraffin within minutes, or even, for example, within seconds, at room temperature, i.e. at about 19-25 degrees Celsius or higher, for example up to 40 degrees C. or 60 degrees C. The reagent forming layer may be selected based on the physical properties, including the ability to fast diffuse into the embedding medium and thereby dissolving the embedding media. The dissolved embedding medium will thereafter easily be removed or further diluted before removal.

In embodiments where the reagent forming layer is a solvent, the solvent may have, among others, low viscosity, low level of odor, and high stability during storage and use. Low viscosity facilitates delivery of the solvent to the sample, ensures fast spreading of the solvent over the sample and penetration into the tissue, and provides easy removal during the wash cycles.

As used in the present application, a solvent with a low viscosity, refers to a solvent with a dynamic viscosity below 500 cP at room temperature. In some embodiments, solvents or solvent mixtures with a viscosity below 85 cP, such as a viscosity below 30 cP may be used. Non-exhaustive examples of low viscosity solvents are vegetable oils, such as soy, corn, rapeseed, olive or other natural oils having a viscosity ranging from about 25 to 150 cP, whereas their corresponding mono alcohol esters, for example methyl esters, may have a viscosity ranging from 10 to 50 cP or lower.

In at least one embodiment of the present application, the solvent is not chemically reactive to prevent alterations of the sample. In other words, the solvent is chemically unreactive, i.e. stable, in order to prevent alterations of the sample. Generally the solvent is able to hold a high concentration of embedding media, e.g. paraffin, in solution at room temperature. Thus allowing for the use of a minimum volume of the solvent and preventing precipitation of the embedding medium, for example paraffin.

In one embodiment of the present application, the solvent has a high boiling point, low flammability and high or no flash point. In another embodiment of the present application the solvent is non-flammable. Examples of such solvents, e.g. oils, may be used in food applications as, for example, cooking oils; in the pharmaceutical industry for, for example, dissolving and stabilizing drugs; in the cosmetics industry as, for example, emollients; and in the paint industry as, for example, diluents.

In a preferred embodiment, the solvent or agent of the present application is low or non-toxic for humans, as well for the environment in general, to allow for easy destruction and waste handling.

In embodiments, the selection of an appropriate solvent or solvent mixture may be accomplished by using Hansen's solubility model, which summarizes the dispersion, polar and hydrogen bonding properties of the solvent or embedding medium in a 3-dimensional space.

Properties such as density, vapor pressure, evaporation rate, flash point, boiling point, etc., can more easily be tailored to the practical use while still maintaining an acceptable degree of solvency power. Values for each of these parameters for a particular solvent can be obtained from various literature sources. Methods are available in the literature for calculating or estimating the parameters for unusual solvents.

For a solvent or solvent mixture, the resulting point in 3-dimensional space may represent the solubility of the solute, and a roughly spherical shape surrounds the point and defines a 'radius of interaction' (Ir) for the solute. Solvents having 3-dimensional solubility parameters falling within the sphere will, in theory, dissolve the embedding media.

In some embodiments, the solvent will dissolve the embedding medium. The resulting liquid can be removed from the sample. The liquid has a density lower than the aqueous washing buffer used as the carrier layer, and will therefore separate from the sample and float to the surface of the aqueous buffer.

In a preferred embodiment of the present application, the density of the solvent is lower than the density of the carrier composition, e.g. the washing buffer, used to remove the solvent and the dissolved embedding medium. The density of the solvent may be lower than 1.00 g/ml. If, for example, a paraffin embedded biological sample is exposed to the solvent Histo-Clear® having a density to paraffin oil of about 0.84, the resulting Histo-Clear® and paraffin liquid will separate from the sample and lift to the surface of the sample for easy removal when exposed to aqueous washing buffer having a density at approximately 1.00 g/ml or slightly higher due to its salt content. In some embodiments, most of the embedding medium is substituted by solvent and dissolved before the slides are washed with the carrier composition, comprising for example aqueous buffers.

The differences in density of the solvent and the carrier composition enhance the efficiency in separating the embedding medium from the sample. Said density difference may be increased by manipulating, for example, the salt content in the aqueous wash buffer and the exact mixture of the solvent.

According to one embodiment, a two phase system is created in a container or pretreatment tank where after an embedded biological sample on a support is placed into the two phase system. Thereby the solvent for removing the embedding medium will remove the embedding medium of the biological sample, when in contact with the sample. Afterwards the treated biological sample can easily be washed in a separate container to remove any leftover solvent.

According to another embodiment of the application a reagent forming layer, for example a solvent, for removing embedding medium is placed into a container or pretreatment tank, where after a carrier composition is inserted into the container. This results in the transportation of the solvent for removal of embedding medium from the bottom of the container towards the top or upper end of the container or pretreatment tank. The method of transporting the solvent for removing the embedding medium over the embedded biological sample can be varied without departing from the scope of this application. An embedded biological sample on a support, which has been placed in the container, will thereby be in contact with both liquid phases. The reagent forming layer for removing embedding medium, will be in contact with the embedded biological sample and start removing the embedding medium as the reagent forming layer is transported over the embedded biological sample. When the reagent forming layer has passed over the biological sample the lower carrier composition layer essentially functions as a washing solution, rinsing the biological sample free of embedding medium and solvent. After a few minutes incubation, the process of introducing carrier solution into the container can be stopped or repeated e.g. two, three or four times.

When embedding medium has been removed from the embedded biological sample, reagent forming layer, or solvent layer may be in the bottom of the container or at the top of the container. According to one embodiment, where the solvent is in the bottom of the container it can be reused or removed through an outlet in the bottom of the container and any excess solvent can thereafter be rinsed from the biological sample.

According to another embodiment of the application, the volume of the carrier solution can be increased to more than can be contained in the container or pretreatment tank, hence removing most of the reagent forming layer by overflow from the container, for example into a drain. The target retrieval may thereafter be performed in the same container by applying heat and required method steps.

By using the overflow method, the carrier solution can be used as a washing/rinsing solution, reducing the need for added solutions or steps. Furthermore, this method further prevents carryover of solvent for removing embedding medium to other subsequent process steps, and helps minimize cross contamination.

In some embodiments the sample may be rinsed after the deparaffinization with an alcohol or a diluted alcohol solution which may remove any residual solvent. For example, an ethanol solution may be used. Examples of suitable ethanol concentrations are 10% ethanol, 20% ethanol or 30% ethanol in water. These compositions successfully remove any remaining solvent from the sample, but have high enough flash point and boiling point so the risk of fire or explosion is eliminated and the toxicity is reduced. Such an ethanol wash can be done any time after the deparaffinization, but before applying the antibody or probe to the sample.

The two immiscible phase system can be combined with target retrieval in the same container and compared to existing techniques, requires neither the use of xylene nor alcohol. The solvent for removing embedding medium is also called the upper layer, the upper phase, or the upper layer solvent and these terms are used interchangeably. The solvent as used in the present application comprises organic solvents capable of dissolving an embedding medium. Examples of suitable solvents include but are not limited to, hydrogenated naphthalene, naphthenic hydrocarbons, d-Limonenes, paraffinic/isoparaffinic hydrocarbons, paraffinic-glycol etheter, an alkane hydrocarbon, or combinations thereof.

Naphthenic hydrocarbons are sold under the brand names Formula 83™ and Histochoice; d-limonenes are sold under the brand names Americlear, Bioclear, Clearene, Hemo-DE, Histoclear, HistoSolve X, Master Clear and Safsolv. Paraffinic/isoparaffinic hydrocarbons are sold under the brand names Clearify, Clearing 100, Clear Rite 3, Isopar L, Isopar G, Isopar H, Micro-Clear, Micro-Clear-HC, Micro-Clear-R, Paraclear, Safe Clear, Safe Clear II, Shandon XY, Slide-Brite, Xy-Less, XS-3. Paraffinic-glycol ether mixtures are sold under the brand name Pro-Par.

Additional examples of solvents are Histo-Clear® or Histo-Clear® II, which are complex mixtures of higher oils. Histo-Clear® is a trade name for an organic solvent sold by National Diagnostics, Atlanta, Ga. HistoClear ($C_{10}H_{16}$) is a naturally occurring hydrocarbon found in plants. Histo-Clear® may also be known as 1-methyl-4(1-methylethenyl) cyclohexane p-mentha-1,8-diene, d-limonene, Safsolv (brand name, sold by BrodiSpecialty Products, Ltd.), histolene, dipentene. Citrisolv from Fisher Scientific, is a d-Limonene-based solvent may also be used as a safe alternative to xylene and ethyl acetate Clearify™ and Histo-Clear® may be especially useful solvents since many embedding media, such as paraffin, contain higher polymers that are difficult to remove by the use of warm aqueous washing solutions, such as aqueous buffers. Isopar is also very useful as it has limited odor and is relatively inexpensive.

Additional examples of useful solvents are Alkane hydrocarbons, including pentane, heptane, hexane, octane and higher analogous and branched isomers, including dodecane; toluene, chlorobenzene, 1-methylnaphthalene, diisobutyl ketone, biphenyl and various halogenated solvents and mixtures thereof.

Other examples of suitable solvents are oils or mixtures based on animal, vegetable or mineral sources. Vegetable oils may be essential oils and natural oils. The natural oils resemble animal oils and fats. Natural oils are naturally occurring triglycerides of long-chain fatty acids, which are biodegradable and have a low toxicity. Crude natural oils can be refined after extraction by e.g. removing free fatty acids, bleaching and steam stripping under vacuum to remove odor, flavors and some color forming products.

Of possible interest are low or non-toxic solvents or oils, comprising animal and vegetable oils. Vegetable oils can be esters of glycerin and a varying blend of fatty acids. Vegetable oils have low toxicity, and low flammability, and are widely available. Examples of sources for vegetable oils comprise, but are not limited to, oilseeds like cashew, castor bean, coconut seed, flax seed, grape seed, hemp, mustard, poppy seeds, rapeseed, canola, safflower, sesame seed, and sunflower. Additional sources of vegetable oils comprise, but are not limited to, almond, apricot, avocado, maize/corn, cotton, cocoa seed butter, coconut, fusarium, hazelnut, neem, olive, palm and palm kern, peanut, pumpkin, rice, soybean, and walnut.

For example, oils comprise, but are not limited to, oils or mixtures of oils from corn, soybeans, palm, rapeseed, sunflower seed, peanut, cottonseed, palm kernel and olive. Vegetable oils may comprise, but are not limited to, hydrogenated vegetable oils and refined oils and mixtures based on caprylic and capric fatty acids.

In some embodiments of the present application, the solvent may comprise an ester of a vegetable oil. The ester may be a mixed fatty acid ester prepared from alcoholysis of the vegetable oil. Usually, such a mixed fatty acid ester has a lower viscosity and an improved stability against oxidation as compared to the viscosity and stability of the vegetable oil from which it was prepared, whereby the viscosity and the stability of the first solvent may be improved. The resulting products after such esterification or transesterification include for example esters of branched or straight chain primary alcohols with straight chain dicarboxylic acids, esters of branched chain mono-carboxylic acids and straight chain diols or polyalkylene glycols, esters of straight chain primary alcohols with branched chain dicarboxylic acids and esters of neopentyl polyols with monocarboxylic acids.

In other embodiments of the present application, the first solvent may comprise a fatty acid methyl ester (FAME). A fatty acid methyl ester can be created by a catalyzed reaction between fats or fatty acids and methanol. Methyl esters having 8 to 18 carbon atoms are practically non-toxic. For example, the solvent may comprise an ethyl lactate ester, a soy methyl ester, or a soy ethyl ester.

The solvent's stability against degradation, mostly oxidation, can be lowered by adding an antioxidant. Examples of antioxidants comprise, but are not limited to, hindered phenols e.g. butylated hydroxytoluene (BHT) and dibutyl p cresol; certain amines e.g. phenyl alpha naphthylamine; sulphur and phosphorus or compounds containing both of these elements; metal phenates such as the alkaline earth metal compounds of phenol disulphides; zinc compounds of thiophosphates and carbamates e.g. zinc dialkyldithio-phosphate.

Further, radical reactions initiated by ionizing radiation can be reduced by adding to the solvent a compound that absorb in the wavelength range 300 400 nm. Examples of such compounds are hydroxydiphenyl ketones and hydroxyphenylbenzotriazoles.

In embodiments, the solvent or a reagent may comprise a dye, a fluorescent additive, an odorant and/or an anti microbial preservative. By adding a dye or an odorant to the solution, a unique appearance to certain types of reagents, solvents, protocols and instruments may be provided.

Examples of suitable dyes include, but are not limited to, water-insoluble, oil-soluble azo dyes, such as 1-(2,4-dimethylbenzeneazo)-2-hydroxy-naphthalene, which is red; or 2,3-dimethyl-4-(2-hydroxy-1-azonaphthyl)-azobenzene, which is reddish-brown.

Odorants can be added to mask the natural odor of the solvent or reagent in order to improve their acceptability and recognition by the user. These products include substances such as mint, pine and citronella oils. Especially the distinct smell of some natural oils, e.g. citrus-based oils, can be altered by addition of pleasant odorants.

Anti microbial preservatives can be added to the solvent to inhibit microbial growth and thereby prolong the storage life. Examples of suitable artificial preservatives include, but are not limited to, imidazolines, amidoacetals, hexahydrotriazines, oxazolidine derivatives, O-formals, phenoxy alcohols and isothiazolone derivatives.

The carrier composition, carrier fluid, may also be referred as the lower layer, the lower layer solvent, the lower or first phase, or first phase liquid. These terms are used interchangeably throughout this application. Suitable carrier compositions are water and various aqueous solutions, such as buffer solutions or target retrieval solutions. The solvents mentioned herein for both layers may also be utilized for the 4-in-1 process.

According to one embodiment of the present application the carrier composition functions as a washing solution, washing solvents and/or embedding medium from the biological sample. Detergents may be added to the second solution to improve its washing ability.

Rehydration of an embedded biological sample is traditionally done to remove xylene from the biological sample, when xylene is used for removing the embedding medium. However, when using the method of the present application it is not necessary to rehydrate the biological sample. Thus, it is possible to continue directly from removal of embedding medium to for example target retrieval.

In a process where no target retrieval can be performed (for example due to sensitivity of epitope), all embedding medium is removed with the present application, enhancing the performance of the test. When using traditional methods for removing embedding medium usually a small amount of embedding medium is left in the biological sample.

Fixation of biological samples often destroys structure or masks antibodies' binding sites, reducing the antigenicity of small peptides or epitopes. It may be difficult, therefore, to detect epitopes that may be sensitive to formalin fixation by conventional IHC methods. Heat-induced epitope retrieval (HIER) methods may restore antigenicity and have been used successfully to detect a wide variety of antigens in fixed biological samples.

According to one embodiment of the present application, an epitope retrieval solution (also called target retrieval solution) can be used as a carrier composition. Hence, after removal of embedding medium target retrieval can be performed in the biological sample, where the whole or at least a significant part of the biological sample is fully immersed in target retrieval solution. Suitable solutions for use in HIER are for example calcium chelating solutions such as citrate buffer, MES buffer or Tris-EDTA solution.

According to a further object of the present application, the top phase comprising the solvent functions as a lid on top of the target retrieval solution that minimizes evaporation during heating. Hence, condensation in the apparatus, drying out and overheating of the biological sample is reduced.

According to one embodiment of the present application a first solution (solvent or reagent forming layer) and a second solution (carrier composition) are combined to form a two phase system. In an embodiment of the present application, the volume of the reagent forming layer is fixed while the volume of the carrier composition is varied. Thus, when the volume of the carrier composition is increased the phase comprising the first solution travels upwards in the container or pretreatment tank, and when the volume of the carrier composition is lowered the phase comprising the reagent forming layer travels downwards in a container. When a carrier having a biological sample is inserted into the container and the volume of the carrier composition is varied, the phase comprising the reagent forming layer travels up and down over the biological sample. The reagent forming layer removes any embedding medium in the biological sample in the process.

The thickness of the reagent forming layer is dependent on the size of the container, the volume of the second solution and the carrier or support holding the biological sample. Thus, reagent forming layers of different thicknesses are contemplated in this application. According to one embodiment of the present application the thickness of the reagent forming layer can be very small or thin. This leads to a small volume of first solution required, being more environmentally friendly, simpler and reduces costs. In one embodiment the reagent forming layer (also referred to as second phase or solvent layer) may have a thickness of about 1 cm.

One run or pass of the phase comprising the reagent forming over the embedded biological sample generally results in enough deparaffinization, such that the biological sample may be further ready to undergo target retrieval or other process steps. Additional runs or passes to optimize removal of embedding medium are contemplated by the present disclosure.

One embodiment of the present method for pretreatment of embedded biological sample comprise providing a two immiscible phase system with the upper phase capable of lowering the melting point of an embedding medium or dissolving of an embedding medium and the lower phase acting as a carrier solvent; exposing the embedded biological sample to the two immiscible phase system, whereby the embedding medium is liquefied; removing the upper phase by an overflow process; and optionally rinsing the sample with a rinsing solution, e.g. deionized water ("DI water") or target retrieval solution.

Embodiments of the present application further comprise providing a container wherein at least a portion of the two immiscible phase system is provided. Said container, may also referred to as a processing tank, dip tank or a pretreatment tank in the present disclosure. In embodiments, the step of exposing the sample to the two immiscible phase system comprises the step of immersing the sample in the processing tank. In some embodiments, the sample is vertically placed in the processing tank.

Some embodiments of the present application further provide supply means for supplying the two immiscible phase system to the embedded biological sample. The supply means may comprise a source of solvent, a supply nozzle and supply tubing for supplying the solvent from the source to the supply nozzle whereby the solvent can be supplied to the sample through the nozzle. In another embodiment of the present application the reagent forming layer, or solvent, may be introduced into the pretreatment tank through an inlet or a valve.

In some embodiments, the step of exposing the embedded biological sample to the two immiscible phase system comprises the optional step of rinsing the sample with the carrier composition (also referred to as lower layer or carrier layer). The optional rinsing step may be done by the same carrier composition used in the two phase system or by a different one. In some embodiments, the rinsing is accomplished supplying the carrier composition into the pretreatment tank through the inlet or supply means. In some embodiments, the sample is rinsed under a continuous flow of lower or carrier layer for a predetermined time period. According to other embodiments, the sample is rinsed with the lower or carrier layer during several rinsing periods; each rinsing period having a predetermined length of time and two rinsing periods being separated by a non-rinsing period of predetermined length of time. In some cases, after the sample has been rinsed with the two immiscible phase system, the optional rinse step may not be necessary because a sufficient amount of the embedding material will have been removed and the slide sufficiently clean.

The rinsing steps described above, also referred to as a two immiscible phase system rinsing cycle, may be repeated a desired number of times, e.g. two to three times or more.

In embodiments, the two immiscible phase system already supplied to the sample is removed from the sample before the new two immiscible phase system is supplied to the sample.

Embodiments of the present application may also provide mechanical means for the removal of the two immiscible phase system from the container or pretreatment tank. For example, an upper horizontal moving bar that removes the upper layer from the pretreatment container, into for example, a drain. The two immiscible phase system may for example be removed completely or partially by means of an air blower configured to blow the two immiscible phase system off the sample or the solvent may be removed by a suction device configured to suck up the solvent. As an alternative, the air blower may be configured with an additional suction capability whereby the two immiscible phase system may either be blown off or sucked up by the air blower. Further, the two immiscible phase system may be removed by first removing the upper layer by overflow and collection of the upper layer.

In some embodiments, the supply means, e.g. the supply tubing, supply nozzle, inlet, further comprises an air blower or air nozzle for blowing air onto the slide in order to dry the slide or to blow away possible fluid on the slide, e.g. an upper layer, lower layer, two immiscible phase system, or an optional additional washing solution.

In some embodiments, a centrifuge may be used to remove the fluid, e.g. an upper layer, lower layer, two immiscible phase system, or an optional additional washing solution, whereby the fluid is removed by means of the centrifugal force caused by the centrifuge. The centrifuge may be configured to rotate around one or more axes of rotation. The axis of rotation may be an axis in or parallel with the plane of the slide or an axis perpendicular to the plane of the slide.

In some embodiments, the slide is mounted on one or more attachment points or to a fixture, which allows the slide to be slowly or quickly tilted or rotated, to assist efficient removal of liquids from the slide.

In some embodiments, the removal of the fluid from the sample is accomplished by means of the gravitation. The slide with the sample may for example be put in a vertical position whereby the fluid will flow off the slide due to the gravitation or by overflow.

In embodiments, the optional step of providing a washing solution to wash off possible residues of liquefied embedding medium from the sample comprises the step of providing washing solution supply means for supplying the washing solution. The washing solution supply means may comprise a source of washing solution, a washing solution supply nozzle and washing solution supply tubing for supplying the washing solution from the source to the sample via the supply nozzle or inlet. In some embodiments the supply of washing solution and the washing of the sample is automatically controlled. In some embodiments, the solvent supply nozzle and possible also parts of the solvent tubing are configured to function as the washing solution supply nozzle and possible also parts of the washing solution tubing.

According to embodiments, the carrier composition, lower or carrier layer or optional rinsing solution is an aqueous buffer solution capable of removing the liquefied embedding medium and is immiscible with the upper layer. In one embodiment the carrier layer may be DI water. Examples of an aqueous buffer solution are, but not limited to, Tris-Buffered Saline Tween-20 ("TBST"), PBS, Hepes, MES buffer and traditional IHC and ISH target retrieval solutions.

Some embodiments of the present application further comprise optionally rinsing the embedded biological sample with a washing solution comprising a hydrophobic dye, e.g. an azo dye, Sudan Black or Oil Red O before the removal of the embedding medium, i.e., dewaxing or deparaffinization. The dye may be selected such that it gives a high contrast picture by the camera used. For example, the dye may bind non-covalently to both the embedding medium and the tissue. After washing, the embedded biological sample will be colored and the surrounding slide almost uncolored. An image of the colored embedded biological sample and the slide taken by an imaging device, such as a camera, may be analyzed, whereby the colored embedded biological sample can be detected together with its size and location on the slide or support. This information can be used, for example, by a stainer to define reagent drops zones, reagent volumes required, and to ensure the quality of a staining process. The dye is removed during the removal of the embedding medium. The dye can further be used to verify that the removal of the embedding medium, e.g., dewaxing or deparaffinization, and washing was efficient.

Traditionally, a sequence of alcohol treatments was done in order to change from an organic to an aqueous phase in the tissue. The present application provides a method whereby when the removal of the embedding medium is complete the biological sample is in an aqueous environment and the embedding medium has been substituted by an aqueous composition (carrier composition). Hence substantially eliminating the need for a subsequent traditional rehydration step. By substantially eliminating the traditional alcohol steps, the entire process is simplified and consequently the inconvenience of alcohols flammability and toxicity is avoided.

The method of the present application permits reduction of the amount of waste from the dewaxing or deparaffinization process. Moreover, since neither pure alcohol or high concentration alcohol mixtures are generally used in the present application, the nature of the waste is changed and the regulatory and health problems of having large amounts of alcohols are substantially avoided. In addition, by using a non-toxic or low toxic reagent forming layer according to the present application, the pretreatment process of embedded slides is simplified, and safer than traditional removal methods, while preserving at least comparable efficiency.

As mentioned above, embodiments may also comprise an optional rinsing step wherein the sample is rinsed with a rinsing solution such as deionized water or a target retrieval solution.

As mentioned above, a fluid, e.g. a solvent, a washing solution, a rinsing solution or a target retrieval solution, on the slide may be removed from the slide or support in different ways, for example by applied air streams, centrifugal force, gravitational force, flow due to capillary force, by means of suction or by a moving horizontal bar.

In some embodiments, the sample is exposed to a two immiscible phase system, and/or a target retrieval solution when the slide or support is in a vertical position. In such a vertical slide position, the sample is also considered to be in a vertical position. An advantage with embodiments providing deparaffinization on vertical slides, i.e., on slides in a vertical position, using a two immiscible phase system is that cross-contamination or carry-over, which may occur in processing tanks without two immiscible phase systems is substantially avoided or eliminated.

"Cross-contamination" or "carry-over" refers to the process wherein materials are carried into a reaction mixture to which they do not belong. These materials can be either parts of a sample, or reagents. In such cases, carry-over means the transfer of material, e.g. specimen or reagents, from one container, or from one reaction mixture, to another. Carry-over can be either unidirectional or bidirectional in a series of specimens or assays.

In addition, by treating the slides individually, numerous treatment protocols can be run in parallel on many different slides. Also, the slides need not be loaded to a sample processing apparatus e.g. a stainer at the same time—but can be added and removed in a continuous flow process, i.e. slides can be added and removed from the stainer, while the stainer is processing other slides.

In embodiments of the application comprising vertical processing of the slides utilizing a two immiscible phase system, the possibility of cell carry-over from one slide to another is substantially eliminated since the sample slides are generally exposed to a fresh-filtered upper layer or target retrieval solution, and the system of running the two immiscible phase system over the sample slides in the sample holder unidirectionally prevents possible cross-contamination by cell carry-over between slides during the deparaffinization or target retrieval process.

Another advantage of vertical processing of the slides or supports by a two immiscible phase system is that the processing tank does not have to be cleaned between different steps, e.g. between a pretreatment step and further sample processing steps. Accordingly, the processing speed can be increased and the processing time, e.g. the Total Assay Time ("TAT") or the time for processing an assay, can be reduced.

Yet another advantage with embodiments providing deparaffinization on vertical slides by a two immiscible phase system is that the solvent volume required can be reduced. With two immiscible phase system it is, for example, possible to use a smaller volume of solvent per slide as compared to vertical washing using processing tanks without a two immiscible phase system. The volume of the solvent may be less than 10 milliliters per slide and solvent rinsing cycle. For example, the volume of the solvent may be less than 2 milliliter per slide and solvent rinsing cycle. In another example, the volume of the solvent may be less than 300 microliters per slide and solvent rinsing cycle. Furthermore, using vertical processing with a two immiscible phase system, only the side of the slide having the sample needs to be exposed to the two immiscible phase system (reagent forming layer and carrier composition).

It should be understood that methods according to the present application may also be performed at an elevated temperature. In general, the solvency power, i.e., the capability of the upper layer to solubilize or dissolve the embedding medium, will increase with increased temperature. By raising the temperature above ambient temperature during a dewaxing step, the dewaxing will be even more efficient. The first infiltration step of the upper layer through the solid embedding medium may be increased by temperature. An elevated processing temperature may be achieved in different ways. For example, the embedded sample may be heated before the two phase system is supplied, while the embedded sample is exposed to the two phase system; or by heating the supplied fluid before it comes into contact with the sample. In one embodiment of the present application a non-solvent carrier composition may be added into the pretreatment container and heated to a temperature above the melting point of the embedding medium before coming in contact with the sample. Subsequently a cool carrier composition is added to the pretreatment tank, after the embedding medium has melted. Upon coming into contact with the melted embedding medium, the carrier composition cools, and effectively congeals the embedding medium and carries out of the pretreatment tank upon overflow.

In some embodiments, the elevated temperature may be between room temperature and just below the melting point of the embedding medium. The elevated temperature may range from 25 to 60 degrees Celsius. Suitable temperatures may range from 30 to 50 degrees Celsius, and further around 40 degrees Celsius.

The Autostainer™ System (LabVision Corporation) is an example of an automated slide processing system. The stainer is compatible with currently available reagents for staining paraffin-embedded and frozen tissue sections, cytospins, cell smears, and fine-needle aspirates, for example. The stainer is designed to automate manual staining methods routinely used in immunohistochemistry and cytochemistry. Flexible programming allows for an unlimited number of protocols containing up to 35 steps, including rinse and blow steps between different processing steps, and 64 different reagents. A staining run can process from 1 to 48 microscope slides. Individual slides can be programmed to receive different reagents, of specified volume, during any step in a staining protocol, and waste is segregated into hazardous and non-hazardous collection containers, reducing disposal costs. The stainer is further designed to track a variety of data. It can generate patient, reagent, and real-time operation data reports, as well as track reagent usage and log instrument maintenance. In this context the term "reagent" may include any fluid or gas of chemical or biological material applied to a sample carrier, e.g. a slide, including, but not limited to, aqueous mixtures, biological probes, polymerase, antibodies, digestion enzymes, pre-fixatives, post-fixatives, readout chemistry, stain and dyes, markers chromogens, fluorophores, and solvents.

Any traces of paraffin after deparaffination may be carefully monitored on all slides. By taking advantage of paraffin's birefringence (double refraction) it is possible to visualize paraffin residues that would be difficult to detect otherwise in normal bright field microscopy.

In some embodiments, a method for processing slides comprises introducing one or more new slides into a sample processing apparatus, e.g. a stainer, obtaining slide identification information for at least one of the one or more new slides, obtaining a treatment protocol sequence for the at least one of the one or more new slides from a database associated with the stainer using the slide identification information, and processing the new slide according to commands in a command list corresponding to the treatment protocol sequence for the at least one new slide of the one or more new slides. In some embodiments, one or more new slides are introduced into the stainer while the stainer is processing of any old slides previously presented to the stainer.

In some embodiments, a treatment protocol sequence for the at least one new slide may be obtained from the database associated with the stainer by retrieving an individual slide record containing the treatment protocol sequence for the at least one new slide using the slide identification information on the at least one new slide.

In some embodiments, processing the at least one new slide according to commands in a command list corresponding to the treatment protocol sequence for the at least one new slide further comprises creating a list of stainer commands corresponding to individual processing steps in the treatment protocol sequence for the at least one new slide and executing commands in the command list in order on the stainer on the at least one new slide. In some embodiments, processing the new slide according to commands in a command list corresponding to the treatment protocol sequence for the at least one new slide of the one or more new slides is performed autonomously by the stainer.

In some embodiments, slide identification information for the at least one new slide may be obtained by reading a label containing the encoded slide identification information affixed to the at least one new slide. In some embodiments, slide identification may be obtained by reading a glyph or a bar code that contains the encoded slide identification information. In some embodiments, slide identification information for the at least one new slide may be obtained by reading a radio frequency identification tag associated with the at least one new slide.

In some embodiments, the database associated with the stainer may be accessed for other purposes including slide pre-processing, data entry, queries, and report generation concurrent with the processing of any old slides previously presented to the stainer. Slide pre-processing includes creating or updating slide records pertaining to slides in the database associated with the stainer and generating labels containing slide identification information for affixment to slides.

In some embodiments, executing commands in the command list in order on the stainer on the at least one new slide further comprises determining if prerequisites for execution of a next command on the command list have been satisfied, taking corrective action if prerequisites for execution of the next command in order on the command list have not been satisfied, and executing the next command when prerequisites for execution of that command have been satisfied. In some embodiments, executing the next command when prerequisites for execution of that command have been satisfied further comprises applying a reagent to the at least one new slide and updating at least one database record in the database associated with the stainer to reflect the completion of execution. In some embodiments, determining if the prerequisites for execution of the next command on the command list have been satisfied further comprises obtaining information on reagents to be used in executing the next command and determining if an adequate quantity of the reagent is available.

In some embodiments, taking corrective action if prerequisites for execution of the next command in order on the command list have not been satisfied further comprises alerting an operator about prerequisites for the next command that have not been satisfied and monitoring unsatisfied prerequisites for the next command for changes in status.

In some embodiments, updating at least one database record in the database associated with the stainer to reflect the completion of execution further comprises updating at least one database record elected from a group consisting of a slide log to reflect the actions taken on the at least one new slide, a reagent log to reflect the actions taken on a reagent, and a stainer log to reflect the actions taken by the stainer.

Some embodiments of the application also include a method for performing operations over a network on at least one stainer of a plurality of stainers connected in a stainer network (e.g. a LAN), comprising establishing a network connection with the at least one stainer in the stainer network, sending commands to the at least one stainer over the network connection, and receiving responses corresponding to commands sent to the at least one stainer over the network connection. In some embodiments, establishing a network connection with the at least one stainer is initiated from a device within the stainer network.

In some embodiments, establishing a network connection with the at least one stainer in the stainer network further comprises establishing a network connection with an agent within the stainer network, wherein the functions of the agent comprise relaying commands to, and responses from the at least one stainer, and relaying queries to, and returning responses from, a database associated with the plurality of stainers, wherein the database includes information including status information about stainers, slides, consumables, and treatment protocols associated with the plurality of stainers. In some embodiments, the agent is a software tool that also provides a defined interface for an external application through which operations may be performed on the at least one stainer over the network. In some embodiments, the external application is a laboratory information system.

In some embodiments, the operations performed over the network on the at least one stainer include running diagnostic tests and retrieving diagnostic information. In some embodiments, the diagnostic information is used to automatically schedule service on the at least one stainer, if the diagnostic information indicates that such service is to be performed. In some embodiments, the operations performed over the network on the at least one stainer include performing one or more of software and firmware updates.

In some embodiments, the operations performed over the network on the at least one stainer include obtaining information on stainer consumable usage. In some embodiments, information on stainer consumable usage could include aggregate stainer consumable usage for the plurality of stainers. In some embodiments, the information on stainer consumable usage includes reagent usage information and bulk fluid usage information. In some embodiments, the information on stainer consumable usage is used to make a determination regarding the ordering of additional supplies of one or more consumables. In some embodiments, the ordering of additional supplies of one or more consumables is done automatically. In some embodiments, the ordering of additional supplies of one or more consumables is based on an economic order quantity. In some embodiments, the ordering of additional supplies of one or more consumables is based on a predefined plan for the ordering of consumables subscribed to by an entity operating the stainer network.

In some embodiments, the operations performed over the network on the at least one stainer include monitoring the status of slides being processed by the at least one stainer apparatus. In some embodiments, the operations performed over the network on the at least one stainer include obtaining a real-time estimate of the completion time of any of the slides being processed by the at least one stainer. In some embodiments, a real-time estimate of the completion time may reflect the effect of user actions or other unscheduled events such as the introduction or removal of reagent bottles from the stainer, or changing a priority of a slide rack in the stainer, or introducing new slides into the stainer.

In some embodiments, the operations performed over the network on the at least one stainer include obtaining images of samples on slides being processed by the at least one stainer. In some embodiments, the images of the sample may be taken with an appropriate magnification and resolution. In some embodiments, the operations performed over the network on the at least one stainer include obtaining status information pertaining to slides that have not been loaded into the stainer. In some embodiments, all information exchanged with the stainer over the network connection, including all commands sent to the stainer over the network connection and all responses received over the network connection, are encrypted.

Embodiments of the present application also include a method for adaptively scheduling robot tasks in a time interval for a robot coupled to a stainer. In some embodiments, the robot treats slides that are coupled to the stainer according to a treatment protocol using reagents in reagent bottles or fluid containers coupled to the stainer. In some embodiments, the steps in a method to adaptively schedule robot tasks in a time interval comprise creating a robot task list comprising all robot tasks that are ready for execution within the time interval, calculating a robot task priority for each robot task in the robot task list, sorting the robot task list in descending order of robot task priority, and adding robot tasks starting from the top of the sorted robot task list to a robot task execution queue until the robot is fully utilized in the time interval, or the robot task list is exhausted.

In some embodiments, creating the robot task list further comprises adding robot tasks that have been generated as a result of contemporaneous events to the robot task list. The contemporaneous events comprise one or more of introducing new slides into the stainer, adding or removing reagent bottles or fluid containers, and altering a priority assigned to one or more slide racks on which the slides are mounted. In some embodiments, the robot may performs tasks of many types comprising one or more of moving the robot to a position within the stainer, mixing reagents for a slide, applying a reagent to a slide from the reagent bottle or the fluid container, air blowing a slide, tipping a slide to a horizontal or a vertical position; and capturing an image of a slide. In some embodiments, applying a reagent to a slide from the reagent bottle or the fluid container further comprises one or more of applying a buffer to a slide, and applying deionized water to a slide.

In some embodiments, the steps in a method for adaptively scheduling robot tasks in a time interval are performed autonomously by the stainer, which may exercise control over the robot and its operations. In some embodiments, the steps are repeatedly executed for successive time intervals starting from the time at which the stainer is first powered on. In some embodiments, the steps are executed concurrent with the performance of other stainer and robot tasks.

In some embodiments, calculating a robot task priority for each robot task in the robot task list further comprises calculating a score for each robot task based on a mathematical function of sub-scores assigned to individual task parameters. In some embodiments, the individual task parameters further comprise the earliest start time for a task, the latest start time for a task, the time duration to execute the task, the location of the robot, the priority of the rack on which a slide associated with the task is mounted, and a predetermined relative priority for the robot task type. In some embodiments, a predetermined relative priority for a robot task may be one of high or low. In some embodiments, certain robot tasks may be designated highest priority and added directly to the top of the robot's execution queue.

One embodiment of automated sample processing apparatus in which the deparaffinization/dewaxing, as described above, may be employed is illustrated in FIGS. 1-3 and is described below in details. Further aspects and details of this possible embodiment of the automated sample processing apparatus are provided in the following applications and international patent applications, each of which is incorporated by reference herein in its respective entirety: international patent application publication WO 2004/057307 A1, international patent application publication WO 2004/057308 A1, international patent application publication WO 2004/058950 A1, international patent application publication WO 2004/059287 A2, international patent application publication WO 2004/058404 A2, international patent application publication WO 2004/059284 A2, international patent application publication WO 2004/059288 A2, international patent application publication WO 2004/059441 A2, and international patent application publication WO 2004/059297 A1, provisional patent application 60/616,444 and U.S. patent application Ser. No. 11/177,730, and the U.S. patent application Ser. No. 11/229,098 and U.S. Ser. No. 11/227,270.

FIG. 1 shows an exploded view of a pretreatment module 100 for the automatic pretreatment and processing of biological samples. As shown in FIG. 1, a pretreatment module 100 includes a slide rack 104 that contains slides 110, which may contain biological samples 112 needing treatment. In some embodiments, slides 110 are mounted on a slide rack 104, which allow the individual slides 110 to be maneuvered in a vertical position. The slide rack 104 is slid into the internal frame 117. In one embodiment, the internal frame 117 may be open rather than having walls. The bottom of the internal frame 117 optionally has a dispersion grid 114 which may reduce eddy currents or bubbles when the liquid is added for the pretreatment. The rack arm 105 is slid into the rack arm guide 116 of the pretreatment tank 102 with the slide rack 104 in the internal frame 117. The rack arm guide 116 may guide the slide rack to the proper position in the pretreatment tank 102. The pretreatment tank 102 may be temperature controlled by the heating leads 109 which changes the temperature of the heating sheet 107. The heating sheet 107 may be on some or all walls of the pretreatment tank or container 102. Flange 103 may be used for mounting the pretreatment tank or container 102. In one embodiment, after liquid has been added to the pretreatment module 100 above the full amount, the liquid may flow into the overflow channel 113. The overflow channel 113 slopes downward towards the overflow drain 111 to facilitate the removal of the liquid.

Figure 2A:
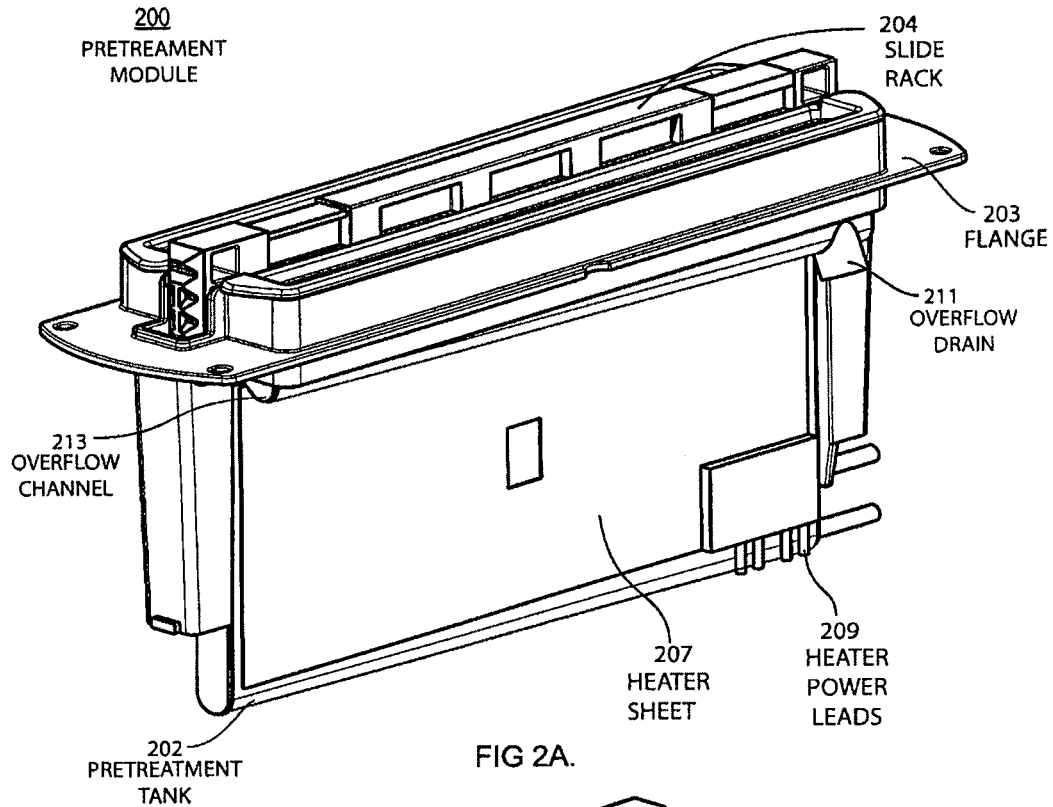
FIG. 2A shows an orthogonal view of a pretreatment module with the slide rack inserted for the automatic pretreatment and processing of biological samples.
Figure 2B:
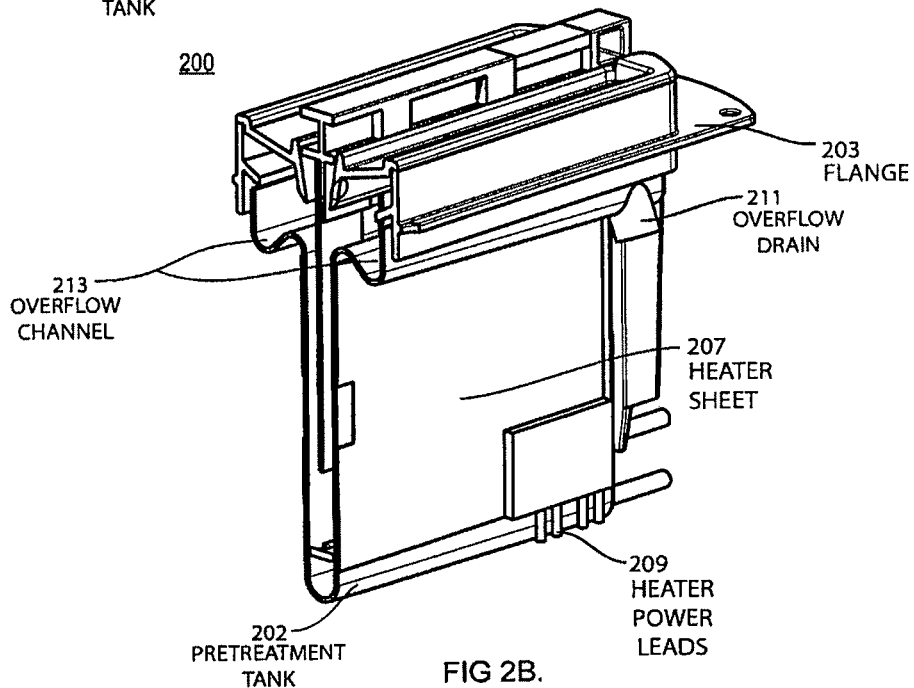
FIG. 2B shows a cross-section view of a pretreatment module with the slide rack inserted for the automatic pretreatment and processing of biological samples.

FIG. 2A shows an orthogonal view of a pretreatment module 200 with the slide rack 204 inserted in the pretreatment tank 202. FIG. 2B shows a cross-section view of a pretreatment module 200 with the slide rack 204 inserted in the pretreatment tank 202. As shown in FIG. 2B, in one embodiment, the overflow channel 213 may allow the liquid when filled to a certain level to be removed from the top of the slide rack 204. The liquid in the overflow channel 213 will be collected in the overflow drain 211 and may be further processed for target retrieval or to recycle the used solvent. The overflow liquid may be the reagent forming layer (or second phase layer) and may comprise paraffin with the target sample. In another embodiment, the overflow liquid may be the first phase liquid (carrier composition) after the second phase layer has already been removed and may comprise an aqueous solvent with the target sample.

Figure 3A:
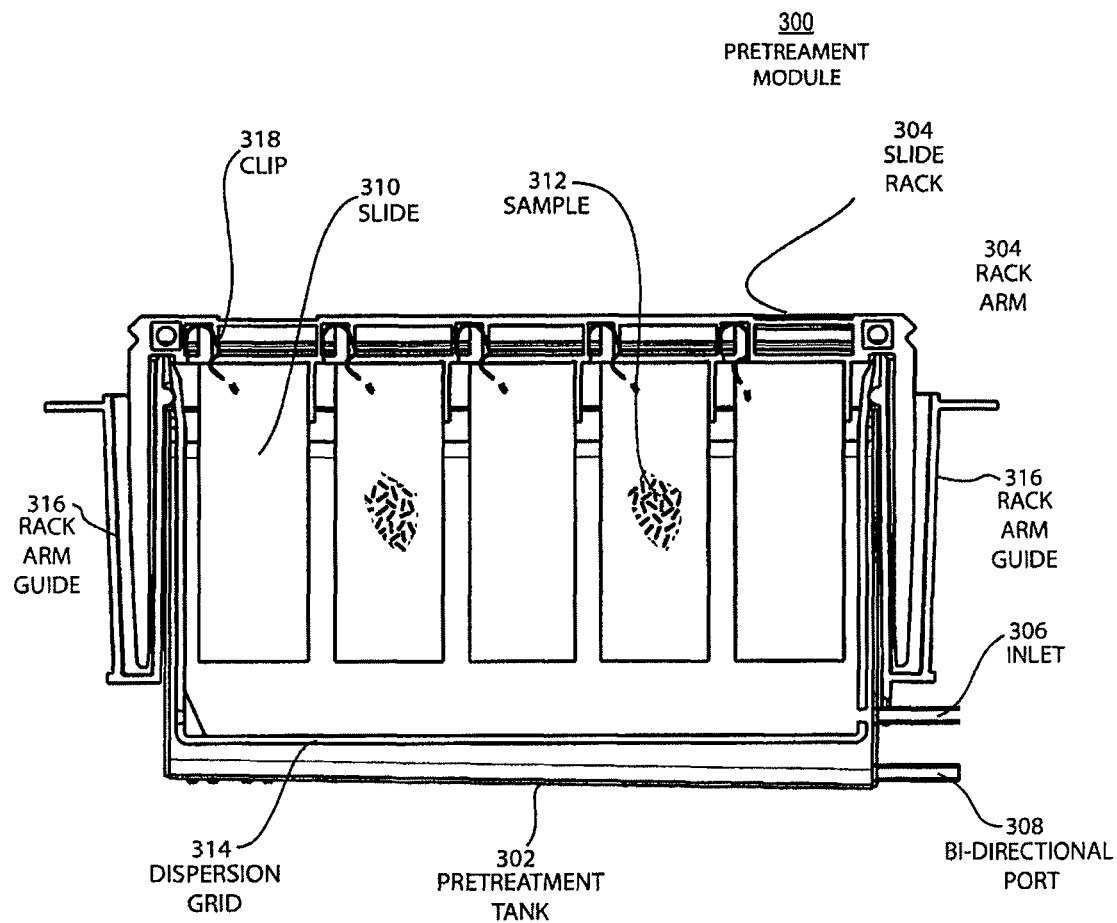
FIG. 3A shows a broadside view schematic of a pretreatment module with the slide rack inserted before the fluid enters the apparatus.
Figure 3B:
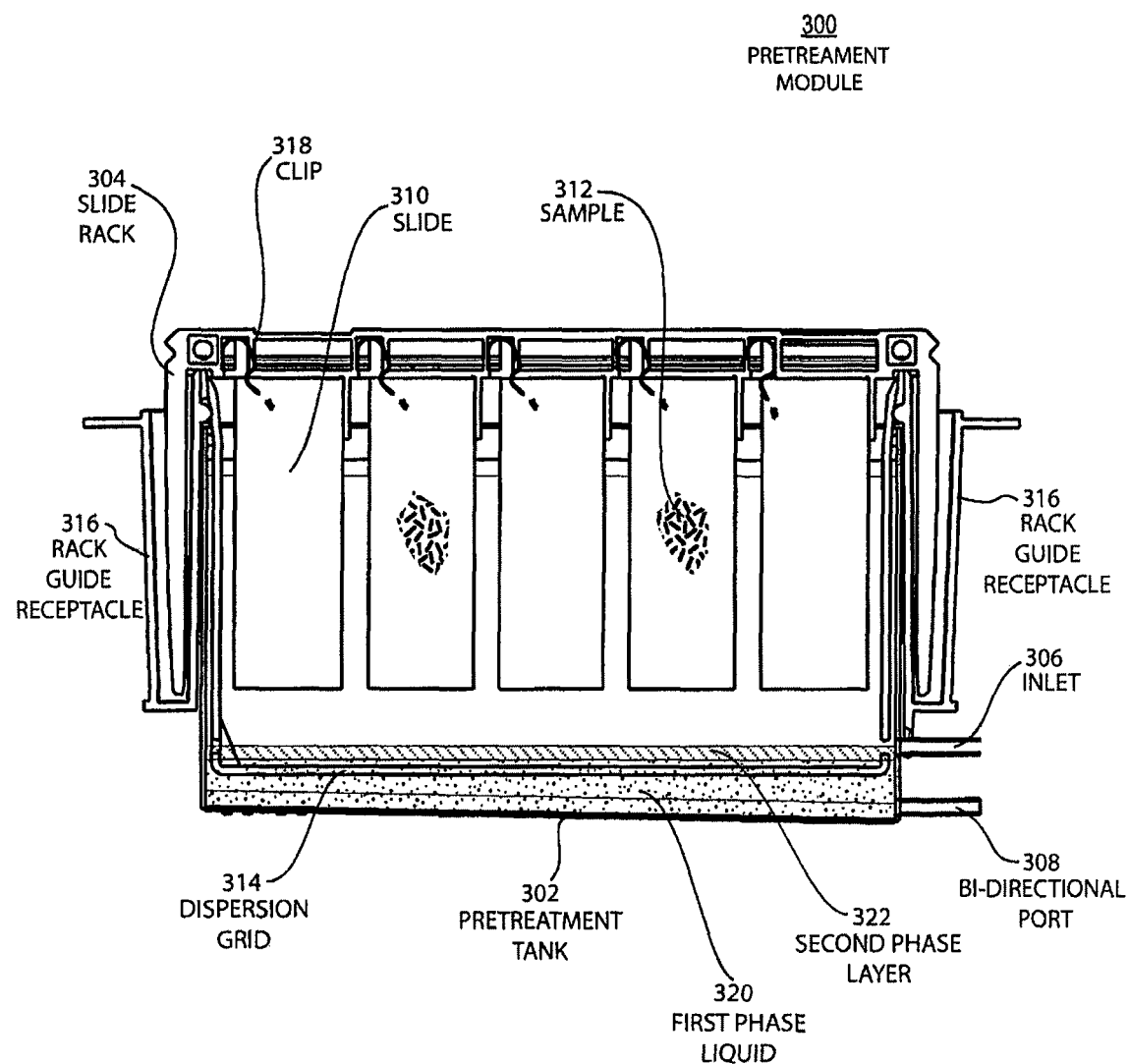
FIG. 3B shows the same a little later, when the thin second phase layer and the first phase liquid is being added to the apparatus.
Figure 3C:
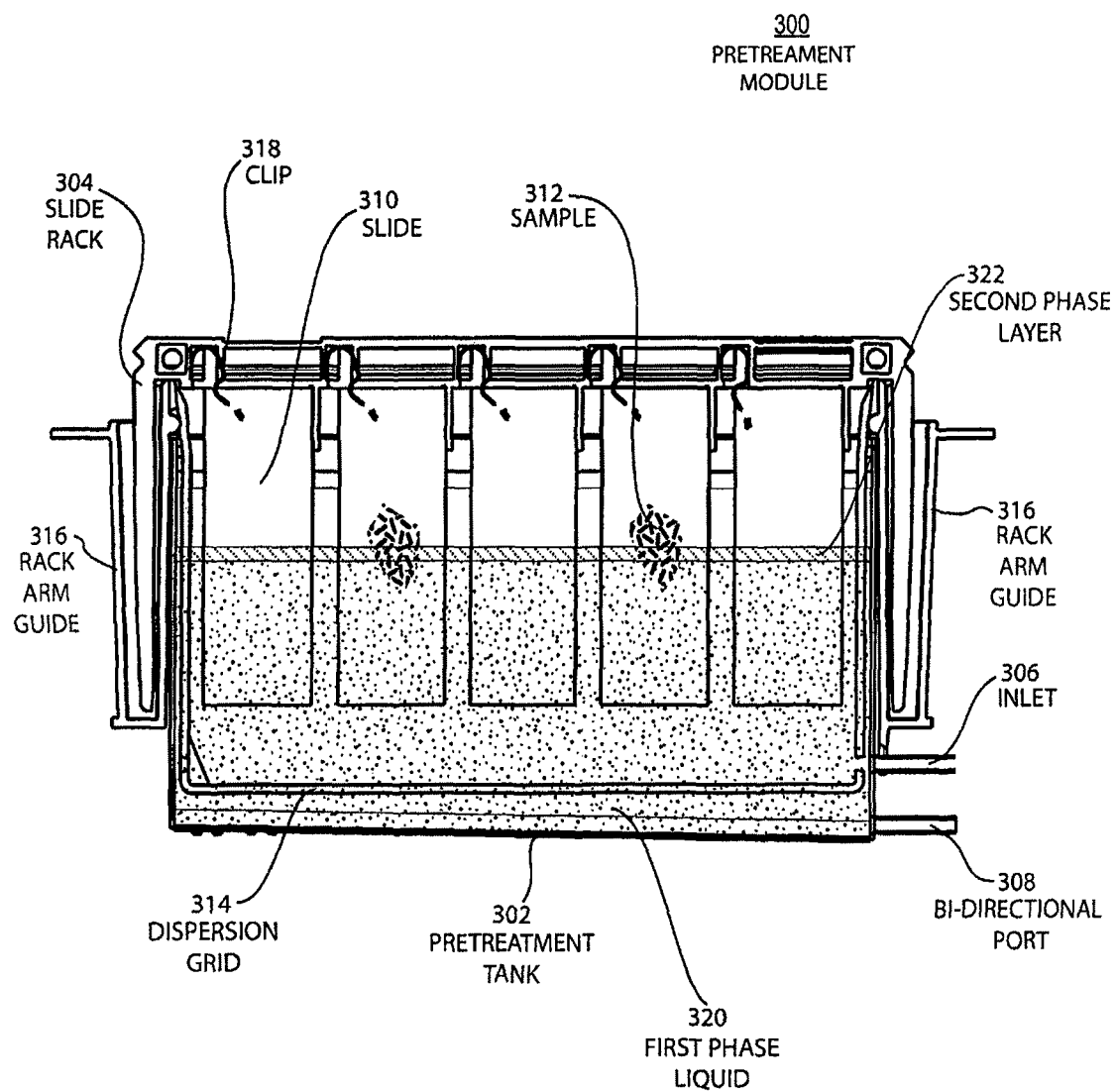
FIG. 3C shows the same a little later, when additional first phase liquid has being added to the apparatus and moves the second phase layer to sweep over the slides.
Figure 3D:
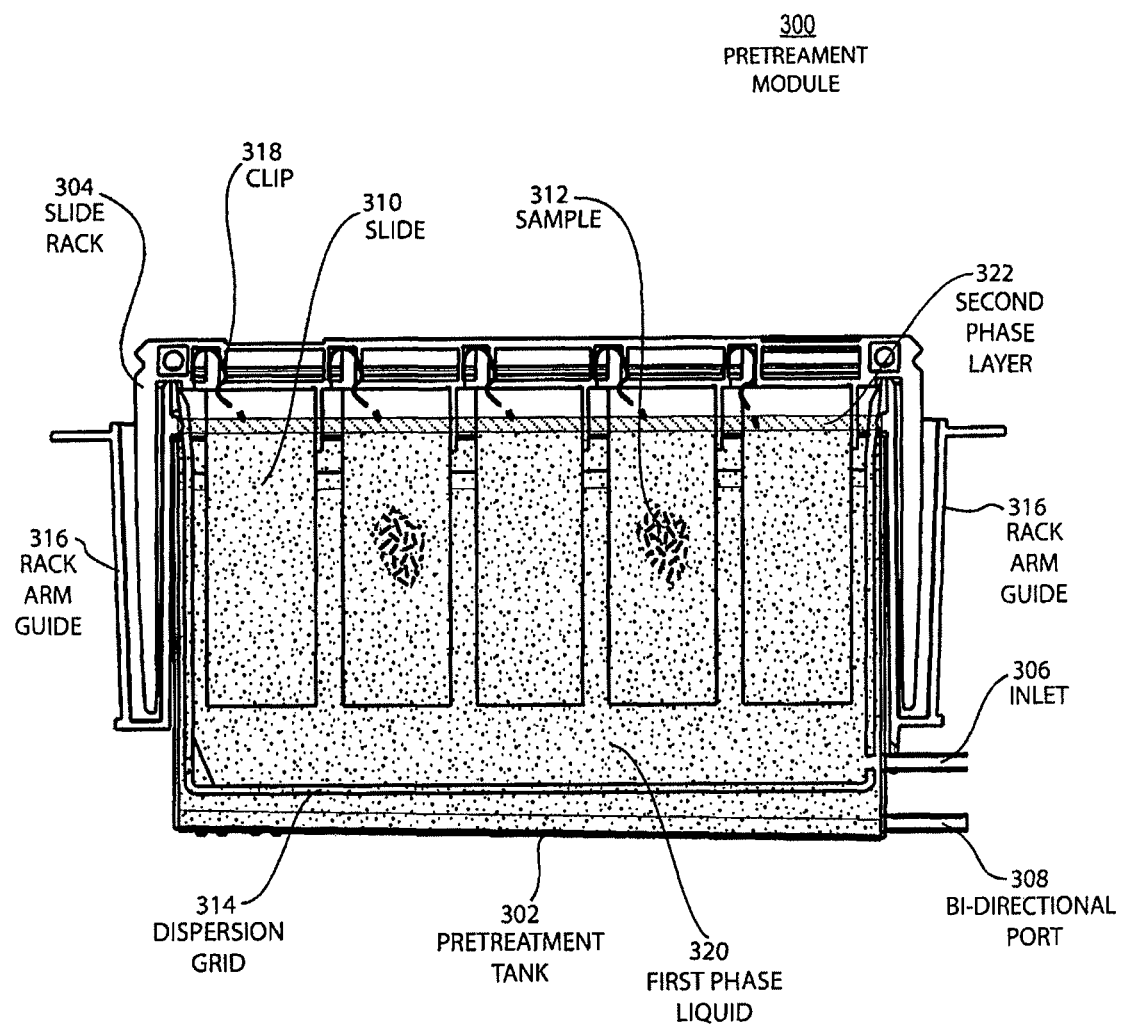
FIG. 3D shows the same a little later, when additional first phase liquid has being added to the apparatus such that the liquid is to the full level but prior to the second phase layer being removed by overflowing.

FIG. 3A-3D shows a broadside view schematic of a pretreatment module 300 with the slide 310 comprising the sample 312 being fastened using a clip 318 to the slide rack 304 which is inserted into the pretreatment tank 302 with the rack guide receptacle 316 acting as a guide for the proper placement. As shown in FIG. 3A, the two phase solvent system has not been introduced into the pretreatment module 300. As shown in FIG. 3B, the thin second phase layer 322 and the thicker first phase liquid 320 are beginning to be introduced into the pretreatment tank 302. The second phase layer 322 is a thin layer which will float on the first phase liquid 320. The second phase layer 322 is added using the optionally unidirectional inlet 306 optionally above the dispersion grid 314 in the pretreatment tank 302. The first phase layer (carrier composition) 320 is being added using the bidirectional port 308 optionally beneath the dispersion grid 314 in the pretreatment tank 302. The optional dispersion grid 314 may reduce the eddy currents or bubbles as the first phase layer (carrier composition) 320 is added to the pretreatment tank 302. The reduction of eddy currents or bubbles allows the two phase system to move up the sample at a uniform rate and level. As mentioned previously, in one embodiment of the present application the second phase layer may comprise the paraffin phase and the first phase liquid may comprise an aqueous phase. As shown in FIG. 3C, additional first phase layer (carrier composition) 320 has been added through the bi-directional port 308. The addition of the first phase layer (carrier composition) 320 sweeps the thin second phase layer 322 upward towards the support or slide 310 to allow for contact with the sample 312. As shown in FIG. 3D, additional first phase liquid has been added through the bi-directional port 308. The addition of the first phase layer (carrier composition) 320 sweeps the thin second phase layer 322 to the top of the slide 310 and the completion of contact between the second phase layer 322 and the sample 312. In one embodiment, the second phase layer 322 may then be removed using the overflow channel (not shown). The first phase liquid 320 may then be removed using the bi-directional port 308 and the slide 310 removed from the pretreatment module 300. In another embodiment, after the second phase layer 322 has been removed using the overflow channel (not shown), a new first phase layer 320 and second phase layer 322 may be added for a fresh second phase layer 322 to be brought in contact with the sample 312. In another embodiment, the first phase layer 320 will be removed using the bi-directional port 308 to sweep the same second phase layer 322 down the slide 310 such that it comes in contact with the sample 312 for a second time. The first phase layer 320 could optionally be added and removed to allow the same second phase layer 322 to be in contact with the sample 312 several times by moving the second phase layer 322 up and down the slide 310. The choice of whether to sweep the second phase layer 322 over the sample 312 once or multiple times may depend, among other things, on the type of sample.

Figure 4:
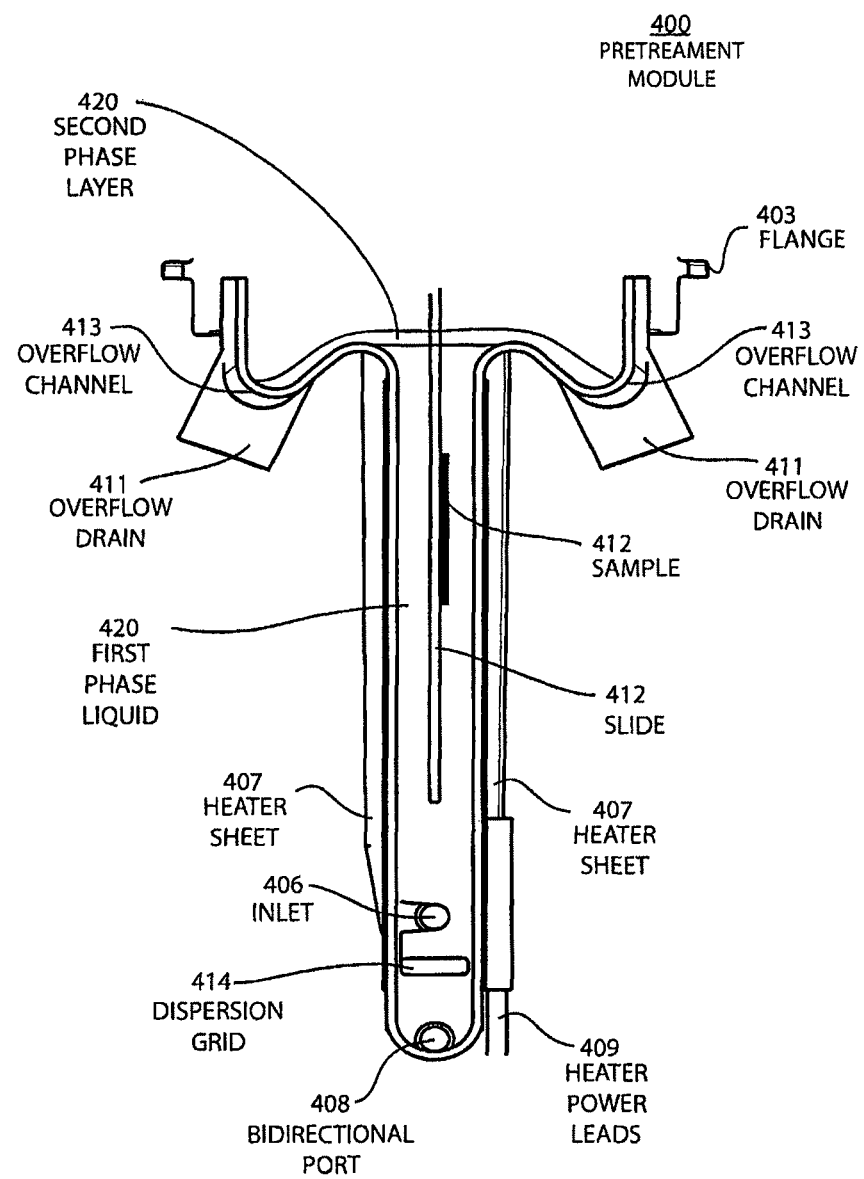
FIG. 4 shows a cross-section view schematic of a pretreatment module with the slide rack inserted when the second phase layer is being removed by overflowing into the overflow channel and the first phase liquid remains in the apparatus.

FIG. 4 shows a cross-section view schematic of a pretreatment module 400 with the slide 412 inserted. As shown in FIG. 4, the first phase layer 420 has been added using the bidirectional port 408 and the second phase layer 420 has been added using the inlet 406 optionally above the optional dispersion grid 414. The pretreatment module 400 may be temperature controlled by using the heater power lead 409 which changes the temperature of the heater sheets 407 on both sides of the pretreatment module 400. As shown in FIG. 4, the second phase layer 420 is above the sample 412 at the top of slide 412 and is of sufficient height to flow into the overflow channel 413. The liquid in the overflow channel 413 may then drain into the overflow drain 411 so that the liquid may be removed. In at least one embodiment, the second phase layer 420 may be removed by overflowing into the overflow channel and the first phase liquid 420 may remain in the pretreatment module 400.

Figure 5:
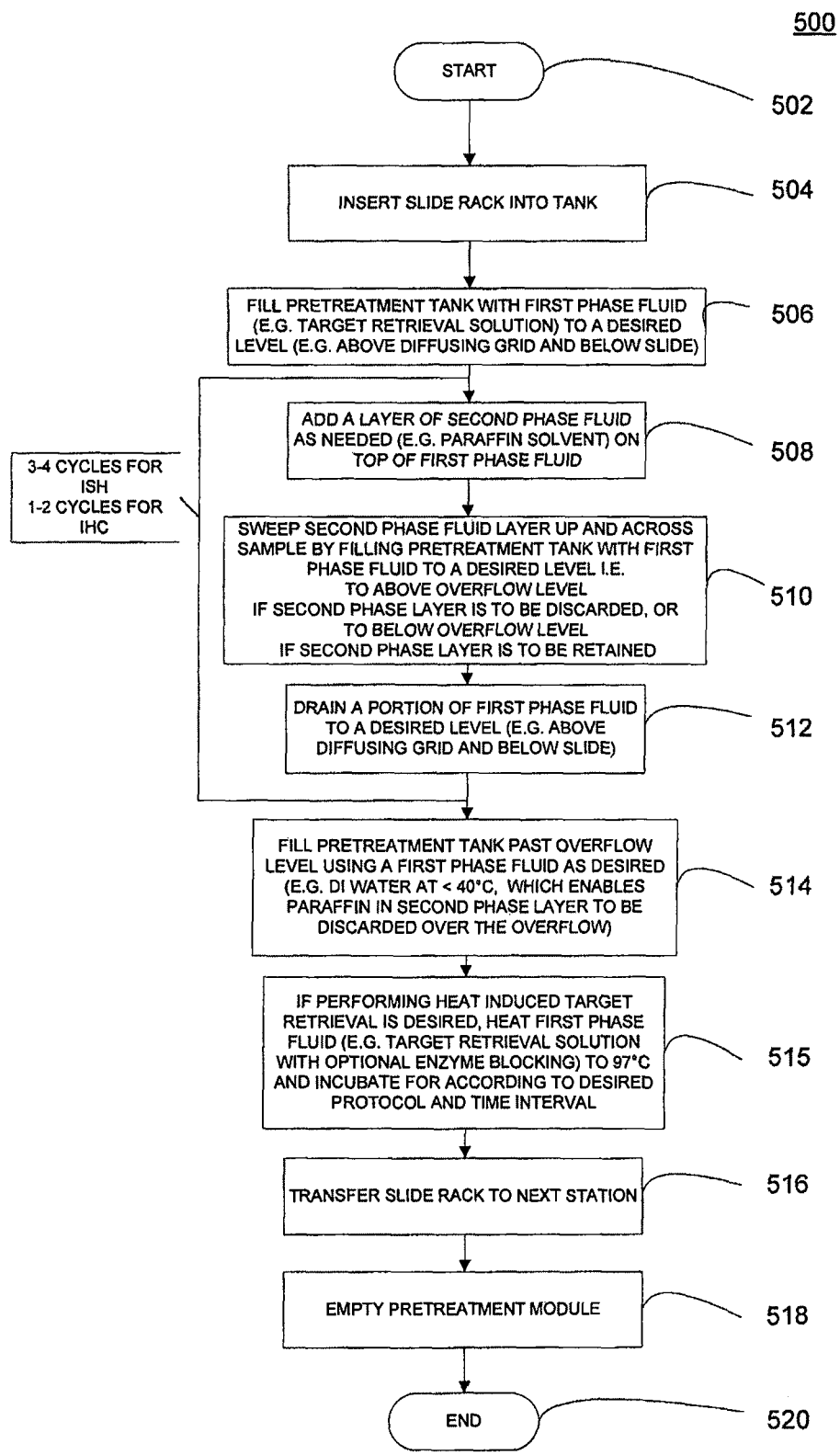
FIG. 5 shows a flowchart of a method for a solvent based two phase pretreatment method.

FIG. 5 shows a flowchart 500 of a method for a solvent based two phase pretreatment method. As shown in FIG. 5, the process begins 502 with the step of the insertion of the slide rack into the tank 504. The pretreatment method may be looped continuously between steps 506 to 512 with the number of cycles changed for ISH and IHC. With the addition of the first phase liquid in step 506, the diffusing grid may optionally be used and the first phase liquid added beneath the diffusing grid. As mentioned above, the first phase layer or carrier composition may be, for example, an aqueous phase which could be used for target retrieval, or DI water with a detergent. After sweeping the second phase layer to the top of the slide in steps 506 to 510, the second phase layer may be optionally removed using the overflow channel between steps 510 and 512. After the pretreatment method has been performed and looped or repeated for a sufficient number of times, the pretreatment tank is filled to above the slide to allow for the second phase layer to be removed using the overflow channel in step 514. In step 515, if a heat induced target retrieval is desired, the first phase fluid which may be the target retrieval solution with optional enzyme blocking can be heated, for example, to about 97 degrees C., and incubated for the desired protocol and time interval. The slides are then transferred from the pretreatment module in step 516 and the pretreatment module is emptied in step 518. The hot slides may prior the transferring from the pretreatment tank to next station in step 516 be cooled down to a temperature that avoid sample damage during the transfer, for example to about 45° C. for a slow transfer or about 65° C. for a fast transfer.

Figure 6:
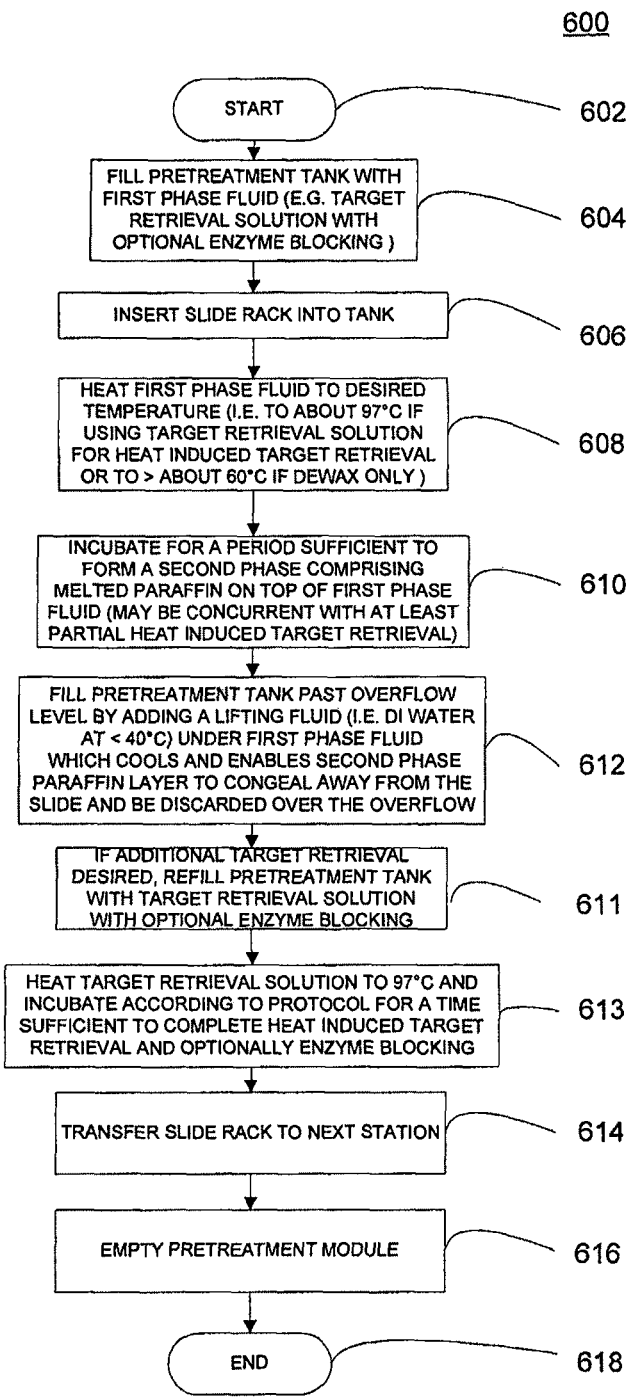
FIG. 6 shows a flowchart of a method for a liquefied paraffin two phase pretreatment method.

FIG. 6 shows a flowchart 600 of a method for a liquefied paraffin two phase pretreatment method. As shown in FIG. 6, the process begins with the addition of the first phase liquid in step 604. The slide rack is then inserted in step 606 and the pretreatment module is heated. The heating of the pretreatment module allows for the heating of the first phase fluid and/or the melting of the paraffin which forms a second phase layer on top of the first phase layer. In one embodiment, the first phase fluid is heated to 97 degrees C. as in step 608 which also allows for target retrieval. In another embodiment wherein heat is used for embedding medium removal, e.g., dewaxing, the first phase fluid or carrier composition is heated to about 60 degrees C. in step 608. Steps 608 and 610 are shown in this figure as two separate steps, however, in one embodiment, these two steps may be combined. The first phase liquid may then be added past the overflow in step 612 to allow for the removal of the second phase layer by overflowing into the overflow channel. In one embodiment, steps 604 to 612 may be repeated as needed to ensure the removal of the paraffin or other embedding medium. In one embodiment, step 611 may be performed for additional target retrieval by refilling the pretreatment tank with target retrieval solution which may comprise optional enzyme blocking. In one embodiment, step 613 encompasses heating the first phase fluid, which may be the target retrieval solution with optional enzyme blocking, to about 97 degrees C., and incubated for the desired protocol and time interval. This may allow for the completion of the heat induced target retrieval and optional enzyme blocking. After the pretreatment method has been performed and looped or repeated for a desired number of times, the slides may then be transferred from the pretreatment module in step 614 and the pretreatment module is emptied in step 616. The hot slides may prior the transferring from the pretreatment tank to next station in step 614 be cooled down to a temperature that avoid sample damage during the transfer, for example to about 45° C. for a slow transfer or about 65° C. for a fast transfer.

Figure 7:
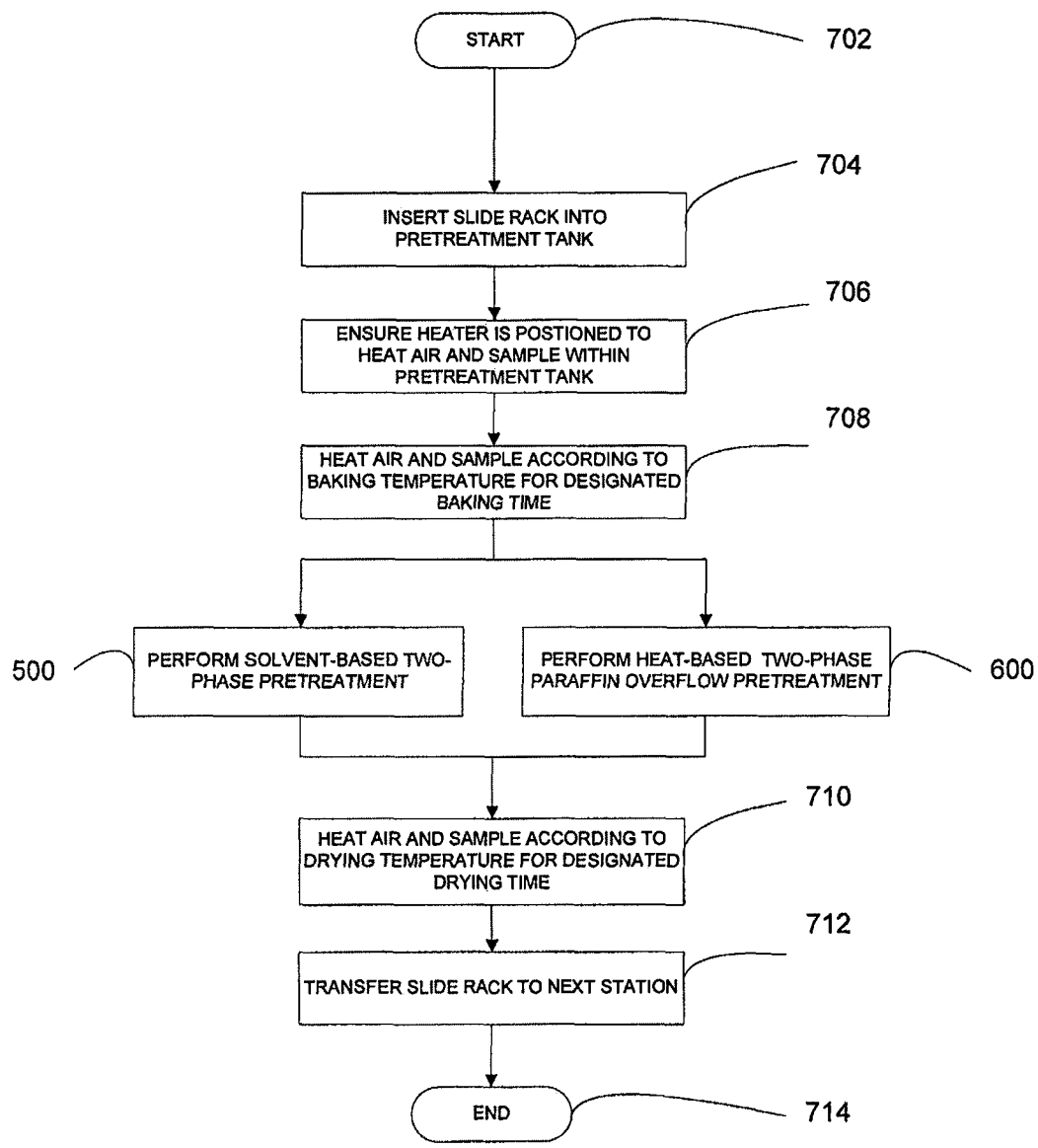
FIG. 7 shows a flowchart of a pretreatment method with baking and drying.

FIG. 7 shows a flowchart 700 of a pretreatment method with baking and drying. As shown in FIG. 7, the process begins 702 with the insertion of the slide rack 704 and ensuring that the heater is positioned to heat the hair and sample within the pretreatment tank 706. The air and sample are then heated for a designated amount of time in step 708 to bake the sample. The sample may be baked to improve the adherence of the sample to the slide. Improving the adherence of the sample may prevent the untimely removal of the sample during later pretreatment steps. The sample may then be processed either by the solvent-based two phase pretreatment 500 or the heat-based two-phase paraffin overflow pretreatment 600, previously shown in FIGS. 5 and 6, respectively. After the sample has been processed, the air and sample are heated for a designated amount of time to dry the sample or slide in step 710. The slide rack is then transferred to the next station in step 712.

Figure 8:
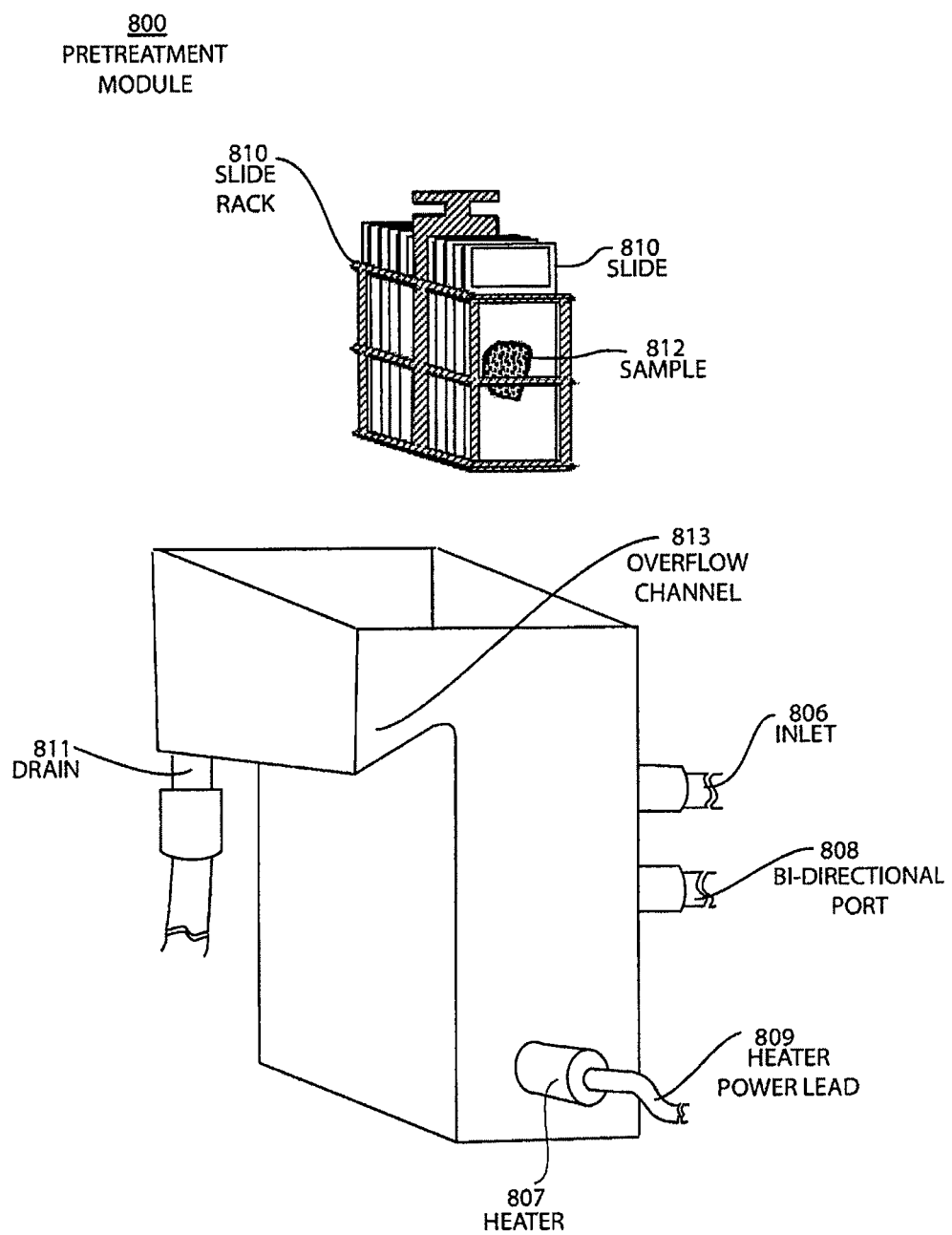
FIG. 8 shows a side-view of a pretreatment module with the slide rack outside of the module for the automatic pretreatment and processing of biological samples.

FIG. 8 shows a side-view of a pretreatment module 800 with the slide rack 810 outside of the module 800 for the automatic pretreatment and processing of biological samples. The slide rack 810 containing vertical slides 810 and samples 812 may be inserted into the pretreatment module 800. The pretreatment module contains an overflow channel 813 connected to a drain 811 for removal of liquids in the pretreatment module and a heater power lead 809 connected to a heater 807 for temperature control. The first phase liquid (not shown) is added by the bi-directional port 808 and the second phase layer (not shown) is added by the optionally unidirectional inlet 806.

Figure 9:
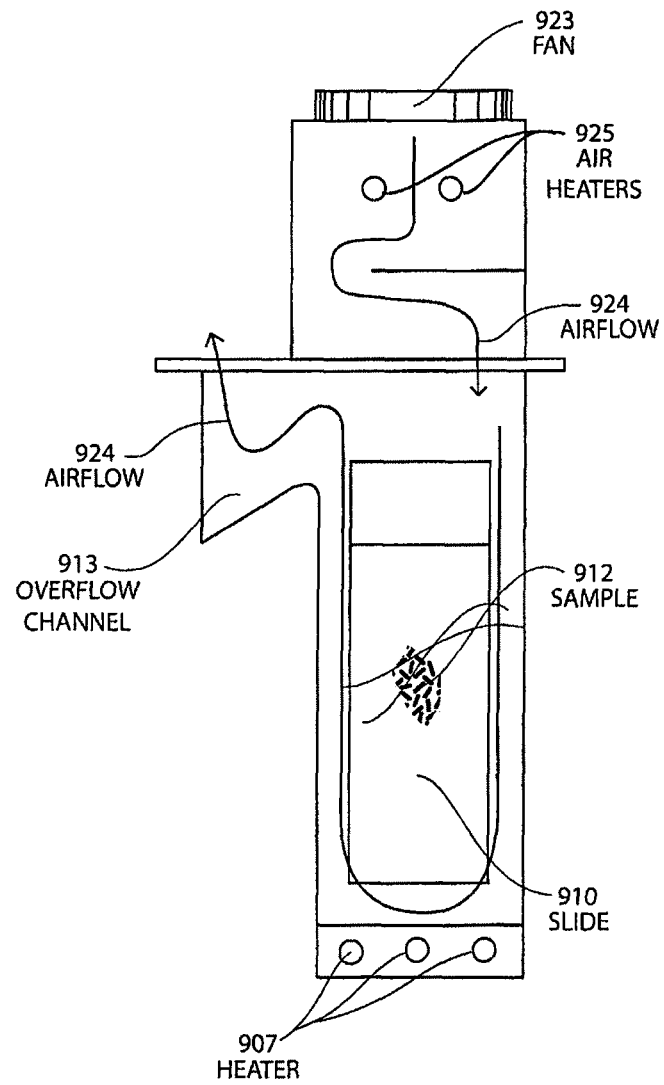
FIG. 9 shows a cross-section view schematic of a pretreatment module showing the airflow around the inserted slide for the pretreatment method with baking and drying.

FIG. 9, shows a cross-section view schematic of a pretreatment module showing the airflow around 924 the inserted slide 910 for the pretreatment method with baking and drying. A fan 923 may force air into the pretreatment module and the air may be heated by the air heaters 925. The air, optionally heated, has an airflow 924 around the slide 910 containing sample 912. The airflow 924 pathway may take the air to the overflow channel 913 where the airflow leaves the pretreatment module. The optionally heated air may allow for the drying of the sample 912 or slide 910. This may allow the slide 910 to be dry when removed from the pretreatment module. The slide 910 and the sample 912 may also be baked to improve the adherence of the sample 912 to the slide 910. The baking in the pretreatment module may be performed by the heater 907.

Various modifications to the embodiments described will be readily apparent to those skilled in the art and generic principles disclosed herein may be applied to other embodiments. The described examples are exemplary only and embodiments described herein are not intended to limit the present application. As such, the claims are to be accorded the widest scope consistent with the principles and features described herein. All patents, patent applications, and other publications are hereby incorporated by reference in their entirety.

EXAMPLES

The examples are performed as according to the General FISH and/or CISH Method or the General IHC Method as described below. Any specific variations in parameter are mentioned in the examples General FISH and/or CISH Method:

The General Method can be performed both manually and in an automated setup. An example of an automated setup is demonstrated in the present application.

1. Deparaffinization—see test conditions in examples.
    Manual deparaffinization—add carrier composition to a container and thereafter add solvent to the container. The solvent will 'float' on top of the carrier composition. Insert slide(s) or slide rack, slowly into the layered content of the container. Raise and lower the slide(s) or slide rack as many times as mentioned in the example. Continue with rehydration if required.
    Automated deparaffinization—in an automated setup fill carrier composition to below a solvent inlet. Apply solvent (clearifying/dewaxing agent) through solvent inlet. Also possible to move slide or slide rack up and down in an automated manner.
2. Target retrieval can be done if applicable—Traditional method such as e.g. heating MES buffer or Citrate buffer to just below boiling point of water (about 95-100° C.) can be used, and the use of pressure cooker allows for higher temperatures than 100° C. without boiling the tissue. It is also possible to perform target retrieval using sodium thiocyanate at 80° C. We used Pre-Treatment Solution above 95° C. for 10 minutes (from K5599, Dako).
3. Pepsin digestion—traditional method can be used, such as remove excess pretreatment buffer or target retrieval buffer, apply Pepsin (from K5599, Dako) to sample, incubate for 2-6 minutes at 37° C., wash as needed with diluted FISH wash buffer (from K5599, Dako).
4. Dehydration—traditional method such as place slides in a series of ethanol solutions (70%, 85%, 96%) for about 2 minutes in each solution. Air dry afterwards. Alternatively wash with water instead of ethanol and air dry at room temperature at about 45° C.
5. Denaturation and hybridization—traditional methods such as apply probe mix to sample, cover sample with a coverslip and seal edges, incubate for denaturation and hybridization at appropriate temperatures (depends on the composition of the probe mixture and hybridization buffer, for example room temperature, 30° C., 37° C., 40° C., 45° C., 50° C., 52° C., 57° C., 60° C., 65° C., 67° C., 70° C., 75° C., 80° C., 82° C., 88° C., 90° C., 92° C., 95° C.) for overnight hybridization incubation for formamide based hybridization buffer or one hour for IQFISH hybridization buffer.
6. Stringent wash—traditional methods such as wash with a Stringency Buffer (from K5599, Dako) once at room temperature and once at 65° C. for 10 minutes, wash with a Wash Buffer (from K5599, Dako) when performing a FISH assay. When the sample is for CISH the process in SK108 (Dako) and do not perform steps 6 below.
7. Dehydration—traditional method such as place slides in a series of ethanol solutions (70%, 85%, 96%) for about 2 minutes in each solution. Air dry afterwards.

Alternatively wash with water or buffer instead of ethanol and air dry at room temperature at about 45° C.
8. Mounting—mounting the sample in a mounting medium, such as Fluorescence Mounting Medium (from K5599, Dako).

General IHC Method:

The General Method can be performed both manually and in an automated setup. An example of an automated setup is demonstrated in the present application.
1. Deparaffinization—see test conditions in examples.
   Manual deparaffinization—add carrier composition to a container and thereafter add solvent to the container. The solvent will 'float' on top of the carrier composition. Insert slide(s) or slide rack, slowly into the layered content of the container. Raise and lower the slide(s) or slide rack as many times as mentioned in the example. Continue with rehydration.
   Automated deparaffinization—in an automated setup fill carrier composition to below a solvent inlet. Apply solvent (clearifying/dewaxing agent) through solvent inlet. Also possible to move slide or slide rack up and down in an automated manner.
2. Target retrieval can be done if applicable—
   a) When using a solvent, traditional method such as heating the sample in a MES buffer or Citrate buffer to just below boiling point of water (about 95-100° C.) can be used, and the use of pressure cooker allows for higher temperatures than 100° C. without boiling the tissue. Some epitopes cannot tolerate target retrieval and proteinase K treatment typically replaces the target retrieval step.
   b) When using 3-in-1 follow procedure in package insert in S2375 (Dako).
3. Staining can be done following the protocol for FLEX (K8000, Dako) or FLEX+ (K8002, Dako).

An example of the used principles:
Enter target retrieval (TR) buffer into bottom of a tank
Enter solvent (e.g. Clearify™, Histoclear II®, Isopar G™) on top of TR buffer, liquid position 1 (this will make a two-phase system)
Fill tank with TR buffer
Empty tank to liquid position 1, leaving a thin layer of solvent over the sample
Incubate for 0-3 min. Some samples can require heating (e.g. to 40° C. or 50° C.)
Overfill tank with TR buffer or water (solvent runs out in overflow drain)
Incubate at 97±2° C. for e.g. 10 min
Cool flush with DI water to <40° C. (remaining solvent if any, runs out in overflow drain)
Transfer slides to staining module for further processing: ISH digestion, IHC staining, special staining and hematoxylin staining.
*n=0-5 cycles, depending of the further processing.

Example 1

This experiment was performed to reconfirm that a manual performed (by hand) 2-phase deparaffinization worked with the Dako standard formamide HER2 FISH pharmDx™ when compared to a traditional xylene processing. The target retrieval step was performed with MES-buffer in a microwave oven.
Enter DI water into a container
Enter solvent (Histoclear II®) on top of DI water (forming a two-phase system)
Dip slide through 2-phase system
Remove slide from 2-phase system
Incubate for 2 min
Wash 2×3 min in wash buffer
Target retrieval in microwave oven for 10 min
Continuing with standard procedure
Conclusion: The manual performed 2-phase deparaffinization worked on Dako's FISH and CISH using the traditional formamide buffer. Rest (droplets) of Histoclear was present on the slides in too high level (there was no removal of Histoclear before TR step).

Example 2

This experiment was to test if a manual performed (by hand) 2-phase deparaffinization worked with the HER2 IQFISH PharmDx™ buffer when compared to traditional xylene processing. The target retrieval step was performed in a microwave oven. Please be aware the CISH protocol used is very hard to the tissue.
Enter DI water into container
Enter solvent (Histoclear) on top of DI water (2-phase system)
Dip slide through 2-phase system
Remove slide from 2-phase system
Incubate for 2 min.
Wash 3×3 min in wash buffer
Target retrieval in microwave oven for 10 min
Continuing with the FISH/CISH procedure
Conclusion: The manual performed 2-phase deparaffinization worked on Dako's FISH and CISH using HER2 IQFISH PharmDx™ buffer. Rest (droplets) of Histoclear II® was present on the slides in too high level (no removal of Histoclear II® before TR step).

Example 3

This experiment was to test if an automatic (FIG. 8-9) 2-phase deparaffinization worked with the HER2 IQFISH pharmDx™ when compared to traditional xylene processing. The target retrieval step was performed by the module.
Version A:
   Enter Di water into bottom of the tank
   Enter solvent (Histoclear II®) on top of DI water (liquid position 1), 2-phase system
   Fill tank with DI water
   Empty tank to liquid position 1
   Incubate for 2 min.
   Overfill tank DI water (Histoclear II® runs out in overflow drain)
   Empty tank
   Fill tank with MES buffer
   Incubate at 97° C. for 10 min
   Cool flush with DI water to 35° C. (remaining Histoclear U® runs out in overflow drain)
   Transfer slides to wash buffer
   Continuing with FISH/CISH procedure
Version B:
   Enter MES buffer into bottom of the tank
   Enter solvent (Histoclear U®) on top of MES buffer (liquid position 1), 2-phase system
   Fill tank with MES buffer
   Empty tank to liquid position 1
   Incubate for 2 min.
   Overfill tank with MES buffer (Histoclear II® runs out in overflow drain)
   Incubate at 97±2° C. for 10 min Cool flush (overfill) with DI water to about 35° C. (remaining Histoclear II® runs out in overflow drain)
Transfer slides to wash buffer
Transfer slides to staining module for further FISH processing.

Conclusion: The automated performed 2-phase deparaffinization using HER2 IQFISH pharmDx™ is as good as or better than those who have had the traditional xylene deparaffinization for FISH staining. CISH stainings were not tested. No rests (droplets) of Histoclear II® was present on the slides (removal of Histoclear II® before and after TR step by module).

Example 4: Various Solvents (FISH and CISH)

The General FISH Method was followed. Specific variations are specified in Table 1.

TABLE 1

Variations in type of solvent, carrier composition, type of probe composition, automated/manual method

| Solvent for deparaffinization | Modifications in method | Results |
|---|---|---|
| Isopar G | Carrier composition is MES buffer (from K5599, dako). Apply 10 µl HER2 IQFISH pharmDx ™ (DAKO, K5731) to sample. Denaturation at 67° C. for 10 min. Automated method, thickness of solvent layer is about 6 mm, incubation time after each cycle (i.e. the solvent is in the bottom of the container) is 1 minute between cycles. Run 3 cycles. | No background, good morphology, clear signals |
| Isopar G | Carrier composition is DI water. Apply 10 µl HER2 IQFISH pharmDx ™ (Dako, K5731) to sample. Denaturation at 67° C. for 10 min min. Automated method, thickness of solvent layer is about 6 mm, incubation time after each cycle (i.e. the solvent is in the bottom of the container) is 1 minute between cycles. Run 3 cycles. | No background, good morphology, clear signals |
| Isopar G | Carrier composition is DI water. Apply 10 µl HER2 IQFISH pharmDx ™ (Dako, K5731) to sample. Denaturation at 67° C. for 10 min min. Automated method, thickness of solvent layer is about 6 mm, incubation time after each cycle (i.e. the solvent is in the bottom of the container) is 2 minute between cycles. Run 1 cycle. | No background, good morphology, clear signals |
| Isopar G | Carrier composition is MES buffer (from K5599, Dako). Apply 10 µl HER2 FISH pharmDx ™ (Dako, K5331) to sample. Denaturation at 82° C. for 5 min. Automated method, thickness of solvent layer is about 6 mm, incubation time after each cycle (i.e. the solvent is in the bottom of the container) is 1 minute between cycles. Run 3 cycles. Followed by CISH procedure (SK108, Dako) | No background, good morphology, clear signals |
| Isopar L | Carrier composition is MES buffer (from K5599, Dako). Apply 10 µl HER2 IQFISH pharmDx ™ (Dako, K5731) to sample. Denaturation at 67° C. for 10 min. Automated method, thickness of solvent layer is about 6 mm, incubation time after each cycle (i.e. the solvent is in the bottom of the container) is 1 minute between cycles. Run 3 cycles. | No background, more difficult to remove solvent from sample than when using Isopar G, morphology impacted, clear signals |
| Clearify ™ | Carrier composition is MES buffer (from K5599, Dako). Apply 10 µl HER2 IQFISH pharmDx ™ (Dako, K5731) to sample. Denaturation at 67° C. for 10 min. Automated method, thickness of solvent layer is larger than the sample and covers the whole staining area (80 ml or about 60 mm in thickness). Incubation time in solvent 10 min. Only one run of solvent over sample, i.e. from bottom and up to the overflow. | No background, good morphology, clear signals |
| Clearify ™ | Carrier composition is MES buffer (from K5599, Dako). Apply 10 µl HER2 IQFISH pharmDx ™ (Dako, K5731) to sample. Denaturation at 67° C. for 10 min. Automated method, thickness of solvent layer is about 4 mm, incubation time after each cycle (i.e. the solvent is in the bottom of the container) is 1 minute between cycles. Run 3 cycles. | No background good morphology, clear signals |

TABLE 1-continued

Variations in type of solvent, carrier composition, type of probe composition, automated/manual method

| Solvent for deparaffinization | Modifications in method | Results |
|---|---|---|
| Histoclear II ® | Carrier composition is FISH wash buffer (from K5599, Dako). Apply 10 μl HER2 FISH probe from Her2 FISH pharmDx ™ Kit (Dako, K5331) to sample. Denaturation at 82° C. for 5 min. Manual method (there is no overflow) | No background good morphology, clear signals., A small residue of solvent identified on the slide. |
| Histoclear II ® | Carrier composition is FISH wash buffer (from K 5599, Dako). Apply 10 μl HER2 IQFISH pharmDx ™ (Dako, K5731)) to sample. Denaturation at 67° C. for 10 minutes, hybridization at 45° C. for 1 hr. Manual method | No background, good morphology, clear signals |
| Histoclear II ® | Carrier composition is MES buffer buffer (from K5599, Dako). Apply 10 μl HER2 FISH probe from Her2 FISH pharmDx ™ Kit (DAKO, K5331) to sample. Denaturation at 82° C. for 5 min. Automated method | No background, good morphology, clear signals |
| Histoclear II ® | Carrier composition is DI water. Apply 10 μl HER2 FISH probe from Her2 FISH pharmDx ™ Kit (Dako, K5331) to sample. Denaturation at 82° C. for 5 min. Automated method. | No background, good morphology, clear signals |
| Histoclear II ® | Carrier composition is MES buffer (from K5599, Dako). Apply 10 μl HER2 FISH pharmDx ™ (Dako, K5331) to sample. Denaturation at 82° C. for 5 min. Automated method, thickness of solvent layer is about 6 mm, incubation time after each cycle (i.e. the solvent is in the bottom of the container) is 1 minute between cycles. Run 3 cycles. Followed by CISH procedure (SK108, Dako) | No background, good morphology, clear signals, a small residue of solvent identified on the slide |

Example 5: IHC

Test Slides (A): Test samples A (see table 2) were automatically pretreated in a module as shown in FIG. 1-4 with EnVision FLEX Target Retrieval Solution, high pH, K8000/K8004 or EnVision FLEX, Low pH, K8005 using the 3-in-1 workflow as specified in the package insert S2375.

After end pretreatment the slides were lowered into room temperature diluted EnVision FLEX Wash buffer, K8007

Test slides (B): Test samples (see table 2) were automatically pretreated in a module as shown in FIG. 1-4 with EnVision FLEX Target Retrieval Solution, high pH, K8004 or EnVision FLEX, Low pH, K8005. The number of solvent cycles were 1, the solvent used was Clearify™ and the cool down volume after TR was 1½ larger than the volume of the container.

Test slides A, B:

Test slides A and Test slides B and reference slides were transferred to an Autostainer. The staining were performed using FLEX RTU antibody specific protocols. After the staining, the slides were dehydrated and mounted permanently.

Conclusion: pretreatment using 2-phase deparaffinization show significantly better staining results to pretreatment using the 3-in-1 method.

TABLE 2 various antibodies tested

| No | Dako Product nr | Name | Tissue for testing | HE* | LE* |
|---|---|---|---|---|---|
| 1 | IR700 | Actin (Muscle) clone HHF35 | Large multi/ Tongue | Colon | Tongue |
| 2 | IR614 | BCL2 Oncoprotein | Large multi | Tonsil | Tonsil |
| 3 | IR625 | BCL6 Protein | Large multi | Tonsil | Tonsil |
| 4 | IR650 | BSAP (Pax5) | Large multi | Tonsil | Tonsil |
| 5 | IR622 | Carcinoembryonic antigen | Large multi | Colon | Tonsil |
| 6 | IR526 | Carcinoembryonic antigen, poly | Large multi | Liver | Pancreas |
| 7 | IR069 | CD1a | Large multi | Tonsil | Tonsil |
| 8 | IR651 | CD2 | Large multi | Tonsil | Tonsil |
| 9 | IR503 | CD3 | Large multi | Tonsil | Tonsil |

TABLE 2-continued various antibodies tested

| No | Dako Product nr | Name | Tissue for testing | HE* | LE* |
|---|---|---|---|---|---|
| 10 | IR637 | Epithelial Antigen | Large multi | Colon | Kidney |
| 11 | IR643 | CD7 | Large multi | Tonsil | Tonsil |
| 12 | IR623 | CD8 | Large multi/Spleen | Tonsil | Spleen |
| 13 | IR648 | CD10 | Large multi | Liver | Tonsil |
| 14 | IR062 | CD15 | Large multi | Tonsil | Kidney |
| 15 | IR604 | CD20cy | Large multi | Tonsil | Tonsil |
| 16 | IR608 | CD21 | Large multi | Tonsil | Tonsil |
| 17 | IR602 | CD30 | Large multi | Tonsil | Tonsil |
| 18 | IR610 | CD31, Endothelial Cell | Large multi | Colon | Tonsil |
| 19 | IR636 | CD34 Class II | Large multi | Liver | Liver |
| 20 | IR751 | CD45, Leucocyte Common antigen | Large multi | Tonsil | Brain |
| 21 | IR628 | CD56 | Large multi | Colon | Tonsil |
| 22 | IR647 | CD57 | Large multi | Tonsil | Colon |
| 23 | IR609 | CD68 | Large multi | Tonsil | Brain |
| 24 | IR613 | CD68 | Large multi | Tonsil | Brain |
| 25 | IR621 | CD79þ | Large multi | Tonsil | Tonsil |
| 26 | IR080 | CDX-2 | Large multi | Colon | Pancreas |
| 27 | IR053 | Cytokeratin | Large multi | Liver | Liver |
| 28 | IR620 | Cytokeratin 5/6 | Large multi | Tonsil | Prostate |
| 29 | IR618 | Cytokeratin 7 | Large multi | Pancreas | Pancreas |
| 30 | IR780 | Cytokeratin 19 | Large multi | Pancreas | Pancreas |
| 31 | IR619 | Cytokeratin 20 | Large multi | Colon | Colon |
| 32 | IR051 | Cytokeratin, High Molecular Weight | Large multi | Tonsil | NA |
| 33 | IR072 | D2-40 | Large multi | Colon | Colon |
| 34 | IR059 | Desmin | Large multi | Colon | Colon |
| 35 | IR629 | Epithelial Membrane Antigen | Large multi/breast | Breast | Tonsil |
| 36 | IR654 | ERα clone 1D5 | Cervix | Cervix uteri mucosa | Cervix uteri mucosa |
| 37 | IR506 | Kappa Light Chains | Large multi | Tonsil | Tonsil |
| 38 | IR626 | Ki-67 antigen | Large multi | Tonsil | Tonsil |
| 39 | IR507 | Lambda Light Chains | Large multi | Tonsil | Tonsil |
| 40 | IR633 | Melan-A | Large multi/Skin | Malignant melanoma | Skin |
| 41 | IR079 | Melanosome | Large multi | Malignant melanoma | Malignant melanoma |
| 42 | IR511 | Myeloperoxidase | Large multi | Tonsil | Liver |
| 43 | IR060 | P504S | Prostate adenocarcinoma/Large multi | Prostate adenocarcinoma | Normal prostate (shall be negative) |
| 44 | IR616 | p53 Protein | Large multi | Colon adenocarcinoma | Tonsil |
| 45 | IR068 | Progesterone Receptor | Cervix | Cervix | Cervix |
| 46 | IR514 | Prostate-Specific Antigen | Large multi | Normal prostate and benign prostate hyperplasia | Normal prostate and benign prostate hyperplasia |
| 47 | IR504 | S100 | Large multi | Colon | Pancreas |
| 48 | IR611 | Smooth Muscle Actin | Large multi | Colon | Liver |
| 49 | IR630 | Vimentin | Large multi | Tonsil | Liver |
| 50 | IR527 | Von Willebrand Factor | Large multi | Colon | Liver |
| 51 | IR524 | GFAP | Large multi | Brain | Colon |
| 52 | IR001 | TdT | Thymus | Thymus | NA |
| 53 | IR059 | E-Cadherin | Large multi | Colon | Liver |

*HE = High expression, LE = low expression

Example 6: Improved Deparaffinization

The procedure describe in General IHC Method above was followed. The carrier composition is DI water, the tissue type is tonsil, the incubation time is 2 minutes and incubation temperature is 40° C. The two phase process includes 3 cycles, i.e. 3 times up and 3 times down the slide (6 runs+overflow).

All the slides were manually haematoxylin stained with S3301 for 5 min., washed with DI water, blued with wash buffer for 5 min and mounted with aqueous mounting media Faramount Mounting Medium (S3025, Dako).

Four types of deparaffinization. The two phase process using either Histoclear II or Isopar G, the 3-in-1 deparaffinization (see package insert of S2375 for process and PT101, Dako) and traditional xylene deparaffinization (see package insert for K5599 for process).

Figure 10A:
FIG. 10 shows that tissue samples deparaffinized with the two phase system (FIG. 10a (Histoclear II®) and FIG. 10b (Isopar G)) showed better results than the tissue samples deparaffinized with 3-in-1 buffer (FIG. 10c) and traditional xylene deparaffinization (FIG. 10d).
Figure 10B:
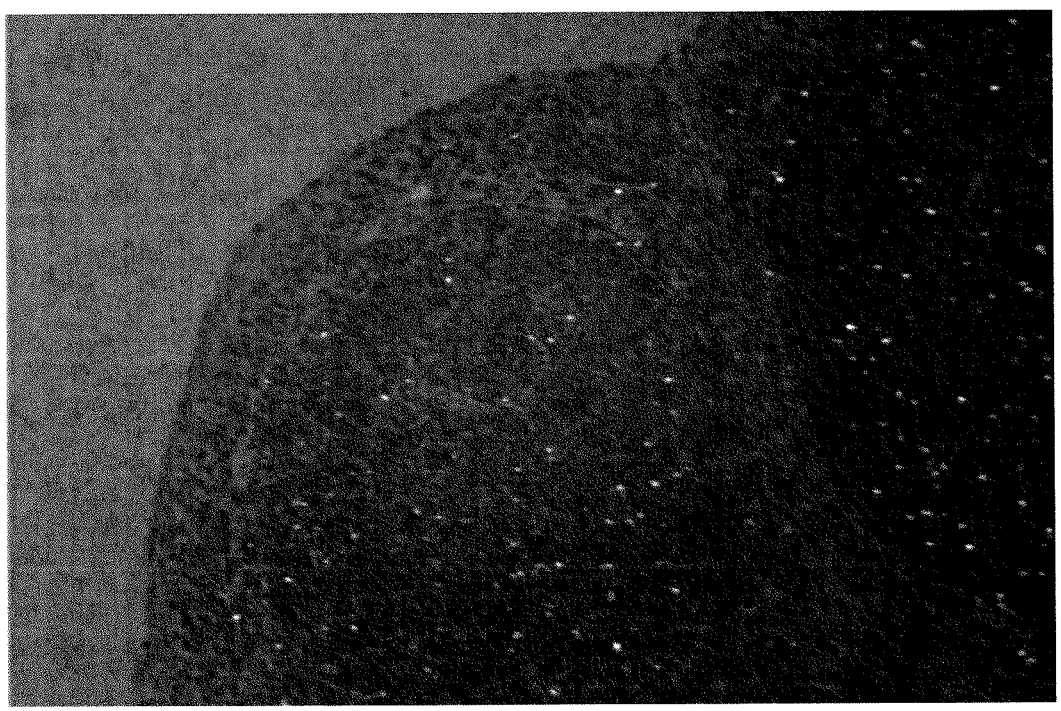
Figure 10C:
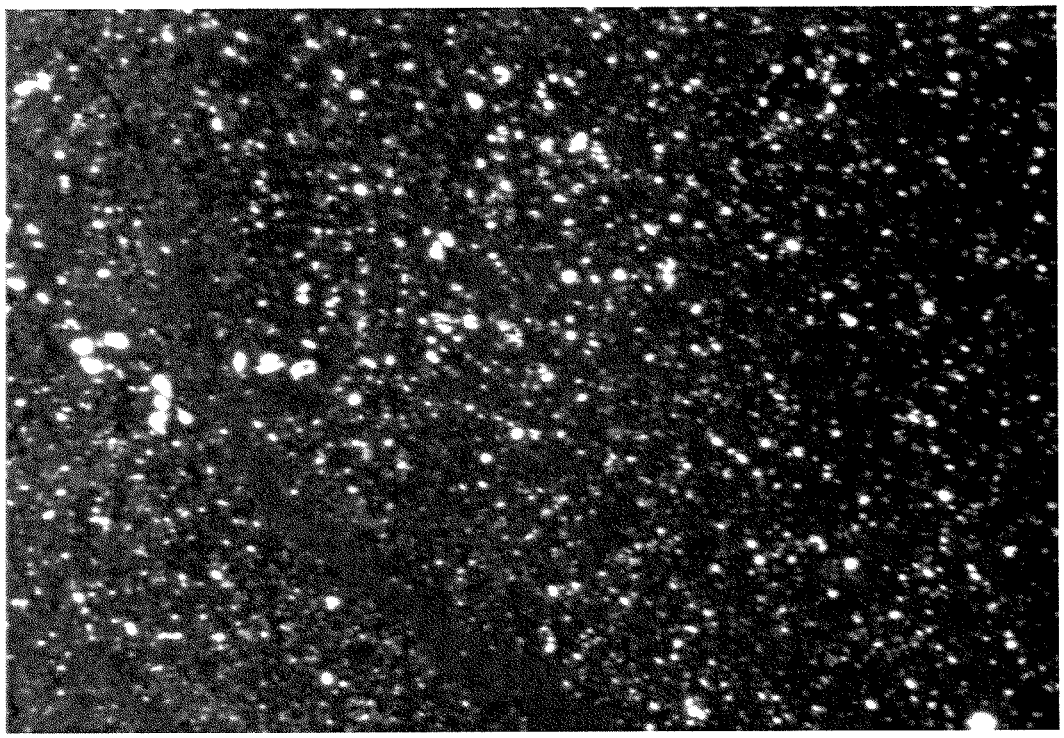
Figure 10D:
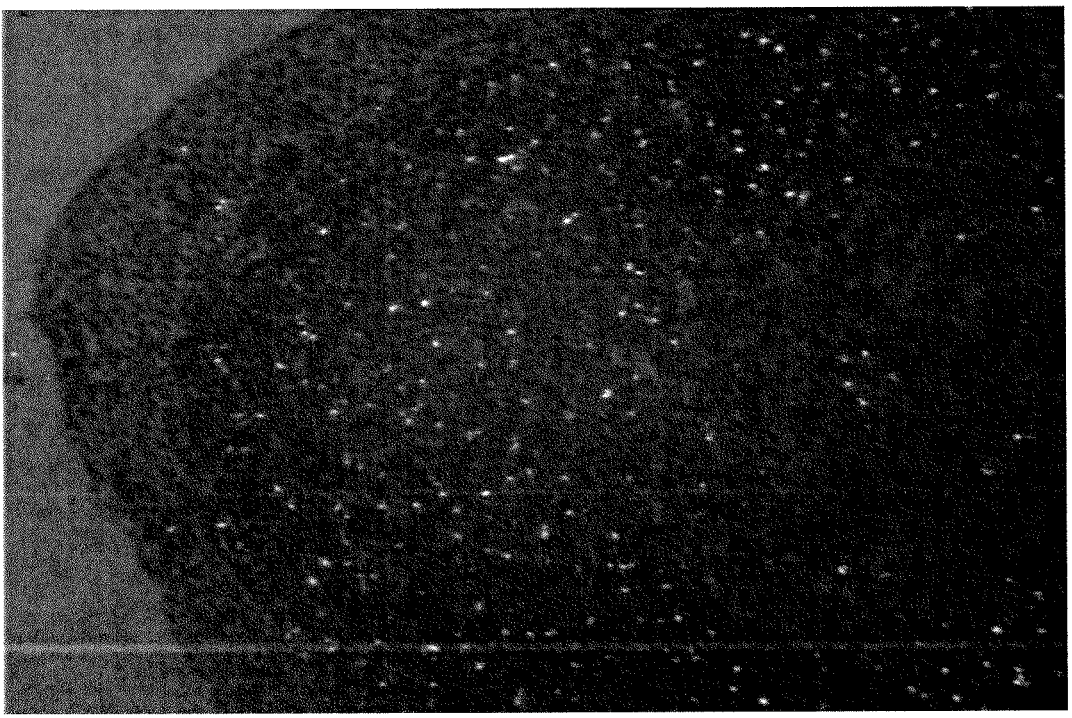

Results: Paraffin residues show up as white/bright spots when visualized with normal bright field microscopy, using polarized filter and mounted with Faramount. The tissue samples deparaffinized with the two phase system (FIG. 10a (Histoclear II®) and FIG. 10b (Isopar G)) showed better results than the tissue samples deparaffinized with 3-in-1 buffer (FIG. 10c) and traditional xylene deparaffinization (FIG. 10d).

Example 7: Amount of Solvent

Various volumes of solvent (upper layer) were tested in order to see if there was an optimum amount that gave the best deparaffinization.

Tests as General FISH and/or CISH Method, using DI water as carrier composition, Her2 IQFISH pharmDx probe (K5731, Dako), automated method.

Number of cycles 4 cycle, incubation time 2 minutes, incubation temperature room temperature.

Histoclear II® was used as the deparaffinizing agent. Volumes tested were 15 ml; 3.0 ml; 4.5 ml; 6.0 ml; 7.5 ml; 9.0 ml and 10.5 ml.

1.5 ml equals about 1 mm thickness of solvent layer, 3.0 ml equals about 2 mm thickness of solvent layer, 4.5 ml equals about 3.0 mm thickness of solvent layer, 6.0 ml equals about 4 mm thickness of solvent layer, 7.5 ml equals about 5.5 mm thickness of solvent layer, 9.0 ml equals about 6 mm thickness of the solvent layer.

Results: all tests showed good paraffinization and better than 3-in-1 when evaluated with dipolarised filter as in Example 6. However, volume above 6.0 ml gave better results than below 6.0 ml, and the 9.0 ml gave the best deparaffinization. FISH staining of the 2-phase deparaffinizations of different thicknesses showed good morphology, low background levels and acceptable signal intensities.

Example 8: Wash with 20% EtOH

Should there be any traces of solvent left on the sample it can be beneficial to wash with a 20% ethanol solution. A wash with a 20% ethanol solution after target retrieval and cool down, showed improved results. The wash was done 2 times with 300 µl of 20% ethanol in DI water, the incubation time in the ethanol solution was 5 minutes. This process showed improved removal of solvent from the sample.

What we claim is:

1. A method for removing at least a portion of embedding medium from an embedded biological sample comprising:
   placing at least one support having an embedded biological sample on its surface into a pretreatment container,
   adding a carrier composition to the pretreatment container,
   adding to the pretreatment container at least one reagent forming a layer on the surface of the carrier composition,
   increasing the volume of carrier composition in the pretreatment container, at least until the at least one reagent forming layer contacts at least a portion of the embedded biological sample, and
   removing at least a portion of the reagent forming layer by increasing the volume of the carrier composition in the pretreatment container.

2. The method according to claim 1, further wherein the carrier composition is added to the pretreatment container after placing the at least one support into the pretreatment container, but before adding to the pretreatment container the at least one reagent forming a layer on the surface of the carrier composition, and further wherein said carrier composition does not contact the embedded biological sample.

3. The method according to claim 1, further wherein the volume of the carrier composition is increased until the at least one reagent forming layer contacts the entirety of the embedded biological sample.

4. The method according to claim 1, further wherein the two phase system is in constant motion whenever it is in contact with the biological sample.

5. The method according to claim 1, further comprising removing at least a portion of the reagent forming layer by increasing the volume of the carrier composition in the pretreatment container until at least a portion of reagent forming layer overflows out of the pretreatment container.

6. The method according to claim 1, further comprising removing at least a portion of the carrier composition from the pretreatment container, such that the reagent forming layer contacts at least a portion of the embedded biological sample a second time.

7. The method according to claim 1, further comprising adding additional carrier composition to the pretreatment container therefore causing the reagent forming layer to contact at least a portion of a biological sample a third time followed by removing at least a portion of the carrier composition thus causing at least a portion of the reagent forming layer to contact at least a portion of the embedded biological sample a fourth time.

8. The method according to claim 1 wherein the reagent forming layer is at a temperature lower than the melting point of the embedding material.

9. The method according to claim 1, wherein the embedding medium is selected from the group consisting of wax, paraffin, paramat, paraplats, peel away paraffin, tissue freezing medium, cryonic gel, embedding compound, polyester wax, and mixtures thereof.

10. The method according to claim 1, wherein the reagent forming a layer comprises a solvent that is capable of dissolving the embedding medium.

11. The method according to claim 10, wherein the reagent forming a layer is selected from the group consisting of hydrogenated naphthalene, naphthenic hydrocarbons, d-Limonenes, paraffinic/isoparaffinic hydrocarbons, paraffinic-glycol ether, an alkane hydrocarbon, and mixtures thereof.

12. The method according to claim 1, wherein the carrier composition is an aqueous buffer solution capable of removing the liquefied embedding medium, and immiscible with the reagent forming layer.

13. The method according to claim 12, wherein the carrier composition is selected from the group consisting of Tris-Buffered Saline Tween-20 ("TBST"), PBS, Hepes, MES buffer, traditional IHC target retrieval solutions, and DI water.

14. The method according to claim 1, wherein the support is selected from a group consisting of a test tube, chip, array, disk and slide.

15. The method according to claim 1, wherein the carrier composition is an aqueous buffer solution capable of removing the liquefied embedding medium, and immiscible with the reagent forming layer.

16. The method according to claim 15, wherein the carrier composition is selected from the group consisting of Tris-Buffered Saline Tween-20 ("TBST"), PBS, Hepes, MES buffer, traditional IHC target retrieval solutions and DI water.

17. The method according to claim 1, further comprising a rinsing steps after removal of the embedding medium with an alcohol or a diluted alcohol solution in water.

18. The method according to claim 17, wherein the diluted alcohol is ethanol.

19. The method according to claim 18, wherein the concentration of the ethanol solution is 30% ethanol or less.

20. The methods according to claim 1 further comprising staining of the pretreated biological samples.

21. The method according to claim 20, further comprising a post staining clearing process.

22. The method according to claim 18, wherein the post staining clearing process comprises exposing a stained biological sample or specimen to a solvent capable of removing embedding medium or a composition capable of removing solvent residues prior to cover slipping.

* * * * *